US012590327B2

(12) United States Patent
Henley et al.

(10) Patent No.: US 12,590,327 B2
(45) Date of Patent: Mar. 31, 2026

(54) COMPOUNDS, COMPOSITIONS, AND METHODS FOR IMPROVING ASSAYS

(71) Applicant: The University of North Carolina at Chapel Hill, Chapel Hill, NC (US)

(72) Inventors: William Hampton Henley, Chapel Hill, NC (US); Elizabeth Ann Dethoff, Chapel Hill, NC (US); John Michael Ramsey, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 465 days.

(21) Appl. No.: 17/048,115

(22) PCT Filed: Sep. 24, 2019

(86) PCT No.: PCT/US2019/052622
§ 371 (c)(1),
(2) Date: Oct. 16, 2020

(87) PCT Pub. No.: WO2020/131182
PCT Pub. Date: Jun. 25, 2020

(65) Prior Publication Data
US 2021/0214776 A1 Jul. 15, 2021

Related U.S. Application Data

(60) Provisional application No. 62/736,525, filed on Sep. 26, 2018.

(51) Int. Cl.
*C12Q 1/6818* (2018.01)

(52) U.S. Cl.
CPC .................................. *C12Q 1/6818* (2013.01)

(58) Field of Classification Search
CPC ................ C12Q 1/6818; C12Q 1/6844; C12Q 2563/131; C12Q 2563/149; C12Q 2565/50; C12Q 2565/101
See application file for complete search history.

(56) References Cited

U.S. PATENT DOCUMENTS

| | | | |
|---|---|---|---|
| 6,143,496 | A | 11/2000 | Brown et al. |
| 6,387,331 | B1 | 5/2002 | Hunter |
| 6,716,629 | B2 | 4/2004 | Hess et al. |
| 6,743,633 | B1 | 6/2004 | Hunter |
| 6,893,877 | B2 | 5/2005 | Hunter et al. |
| 7,332,271 | B2 | 2/2008 | Okeefe et al. |
| 7,547,556 | B2 | 6/2009 | Hunter et al. |
| 8,029,745 | B2 | 10/2011 | Hunter et al. |
| 8,222,047 | B2 | 7/2012 | Duffy et al. |
| 8,236,574 | B2 | 8/2012 | Duffy et al. |
| 8,415,171 | B2 | 4/2013 | Rissin et al. |
| 8,460,878 | B2 | 6/2013 | Walt et al. |
| 8,460,879 | B2 | 6/2013 | Walt et al. |
| 8,492,098 | B2 | 7/2013 | Walt et al. |
| 8,846,415 | B2 | 9/2014 | Duffy et al. |
| 9,110,025 | B2 | 8/2015 | Rissin et al. |
| 9,211,537 | B2 | 12/2015 | Hansen et al. |
| 9,310,360 | B2 | 4/2016 | Duffy et al. |
| 9,329,174 | B2 | 5/2016 | Noji et al. |
| 9,395,359 | B2 | 7/2016 | Walt et al. |
| 9,482,662 | B2 | 11/2016 | Duffy et al. |
| 9,551,663 | B2 | 1/2017 | Rissin et al. |
| 9,617,589 | B2 | 4/2017 | Ramsey et al. |
| 9,678,068 | B2 | 6/2017 | Duffy et al. |
| 9,846,155 | B2 | 12/2017 | Rissin et al. |
| 2002/0094533 | A1 | 7/2002 | Hess et al. |
| 2005/0239108 | A1 | 10/2005 | Barletta et al. |
| 2007/0059690 | A1 | 3/2007 | Islam et al. |

(Continued)

FOREIGN PATENT DOCUMENTS

| EP | 2224015 A1 | 9/2010 |
|---|---|---|
| EP | 1996717 B1 | 11/2014 |

(Continued)

OTHER PUBLICATIONS

Kim, Multiplex real-time PCR using temperature sensitive primer-supplying hydrogel particles and its application for malaria species identification, PLoS ONE, 13(1): e0190451, 2018. (Year: 2018).*

(Continued)

*Primary Examiner* — Gary Benzion
*Assistant Examiner* — Carolyn L Greene
(74) *Attorney, Agent, or Firm* — Myers Bigel, P.A

(57) ABSTRACT

Provided are compounds, compositions, kits, systems, devices, and methods for improving an assay such as, for example, a multiplexed PCR assay (e.g., a multiplexed immuno-PCR assay). A solid support (e.g., a bead) may be provided according to some embodiments of the present invention. The solid support may comprise an encoding agent (e.g., a dye), a nucleic acid sequence (e.g., an oligo-nucleotide and/or primer); and a molecular recognition element (e.g., an antibody). A detection reagent may be provided according to some embodiments of the present invention. The detection reagent may comprise a molecular recognition element (e.g., an antibody) and a nucleic acid tag. In some embodiments, at least a portion of the nucleic acid sequence of the solid support and at least a portion of the nucleic acid target tag of the detection reagent are configured to participate in a nucleic acid amplification process. A solid support and detection reagent may bind to the same target, thereby forming a reagent pair.

14 Claims, 19 Drawing Sheets

(56) References Cited

U.S. PATENT DOCUMENTS

| | | | |
|---|---|---|---|
| 2012/0196774 | A1 | 8/2012 | Fournier et al. |
| 2013/0059741 | A1 | 3/2013 | Weiner |
| 2013/0176767 | A1 | 7/2013 | Brooks |
| 2013/0345078 | A1 | 12/2013 | Walt et al. |
| 2013/0345088 | A1 | 12/2013 | Noji et al. |
| 2014/0094386 | A1 | 4/2014 | Wilson et al. |
| 2014/0272939 | A1* | 9/2014 | Aghvanyan ............ G01N 21/76 435/6.12 |
| 2015/0211048 | A1 | 7/2015 | Ramsey et al. |
| 2015/0353997 | A1 | 12/2015 | Duffy et al. |
| 2016/0060687 | A1* | 3/2016 | Zhu .................... G01N 33/5308 506/31 |
| 2016/0123969 | A1 | 5/2016 | Rissin et al. |
| 2017/0038390 | A1 | 2/2017 | Walt et al. |
| 2017/0160292 | A1 | 6/2017 | Wilson et al. |
| 2017/0234882 | A9 | 8/2017 | Wilson et al. |
| 2018/0003703 | A1 | 1/2018 | Duffy et al. |
| 2018/0017552 | A1 | 1/2018 | Duffy et al. |
| 2018/0037614 | A1 | 2/2018 | Pollock et al. |
| 2018/0163270 | A1 | 6/2018 | Mcdowell-Buchanan et al. |

FOREIGN PATENT DOCUMENTS

| | | | | | |
|---|---|---|---|---|---|
| EP | 2538220 | B1 | 11/2016 | | |
| JP | 2008500047 | A | 1/2008 | | |
| JP | 2010193884 | A | 9/2010 | | |
| JP | 2016512429 | A | 4/2016 | | |
| JP | 2017515469 | A | 6/2017 | | |
| WO | 2005003394 | A2 | 1/2005 | | |
| WO | 2007098148 | A2 | 8/2007 | | |
| WO | 2011143583 | A1 | 11/2011 | | |
| WO | 2013176767 | | 11/2013 | | |
| WO | 2014165061 | A1 | 10/2014 | | |
| WO | 2014182835 | | 11/2014 | | |
| WO | 2015070037 | A2 | 5/2015 | | |
| WO | 2015164212 | A1 | 10/2015 | | |
| WO | 2017015529 | | 1/2017 | | |
| WO | 2017065854 | | 4/2017 | | |
| WO | WO-2017070309 | A1 * | 4/2017 | .......... | C12Q 1/6804 |
| WO | 2017112025 | | 6/2017 | | |
| WO | WO-2017112025 | A2 * | 6/2017 | .......... | G01N 33/542 |
| WO | 2020068174 | | 4/2020 | | |
| WO | 2020162996 | | 8/2020 | | |

OTHER PUBLICATIONS

International Search Report and the Written Opinion of the International Searching Authority corresponding to International Patent Application No. PCT/US2019/052622 (13 pages) (mailed Jul. 14, 2020).

Malou et al. "Immuno-PCR: a promising ultrasensitive diagnostic method to detect antigens and antibodies" Trends in Microbiology, 19(6):295-302 (2011).

Spiro et al. "A Bead-Based Method for Multiplexed Identification and Quantitation of DNA Sequences Using Flow Cytometry" Applied and Environmental Microbiology, 66(10):4258-4265 (2000).

Chang et al. "Immuno-PCR: an ultrasensitive immunoassay for biomolecular detection" Analytica Chimica Acta, 910:12-24 (2016) (Abstract only).

Diehl et al. "BEAMing: single-molecule PCR on microparticles in water-in-oil emulsions" Nature Methods, 3:551-559 (2006) (Abstract only).

Hendrickson et al. "High sensitivity multianalyte immunoassay using covalent DNA-labeled antibodies and polymerase chain reaction" Nucleic Acids Research, 23(3):522-529 (1995).

Hinz et al. "Polymer support for exonucleolytic sequencing" Journal of Biotechnology, 86:281-288 (2001).

Huang et al. "Highly sensitive mutation detection based on digital amplification coupled with hydrogel bead-array" Chemical Communications, 27:4094-4096 (2009).

Kalinina et al. "Nanoliter scale PCR with TaqMan detection" Nucleic Acids Research, 25(10):1999-2004 (1997).

Kan et al. "Isolation and detection of single molecules on paramagnetic beads using sequential fluid flows in microfabricated polymer array assemblies" Lab on a Chip, 12:977-985 (2012).

Leamon et al. "A massively parallel PicoTiterPlate™ based platform for discrete picoliter-scale polymerase chain reactions" Electrophoresis, 24:3769-3777 (2003).

Lind et al. "Development and evaluation of three real-time immuno-PCR assemblages for quantification of PSA" Journal of Immunological Methods, 304:107-116 (2005).

Lizardi et al. "Mutation detection and single-molecule counting using isothermal rolling-circle amplification" Nature Genetics, 19:225-232 (1998).

Margulies et al. "Genome sequencing in microfabricated high-density picolitre reactors" Nature, 437:376-380 (2005).

Nagai et al. "Development of a Microchamber Array for Picoliter PCR" Analytical Chemistry, 73(5):1043-1047 (2001).

Nam et al. "Nanoparticle-Based Bio-Bar Codes for the Ultrasensitive Detection of Proteins" Science, 301:1884-1886 (2003).

Osborne et al. "Single-Molecule Analysis of DNA Immobilized on Microspheres" Analytical Chemistry, 72:3678-3681 (2000).

Rissin et al. "Simultaneous Detection of Single Molecules and Singulated Ensembles of Molecules Enables Immunoassays with Broad Dynamic Range" Analytical Chemistry, 83:2279-2285 (2011).

Rissin et al. "Single-molecule enzyme-linked immunosorbent assay detects serum proteins at subfemtomolar concentrations" Nature Biotechnology, 28(6):595-599 (2010).

Rissin, David M. "Single Molecule Detection: Analytical Applications and Fundamental Studies", Dissertation, Tufts University, 183 pages (Apr. 2007).

Ruzicka et al. "Immuno-PCR with a Commercially Available Avidin System" Science, 260(5108):698-699 (1993).

Sano et al. "Immuno-PCR: Very Sensitive Antigen Detection by Means of Specific Antibody—DNA Conjugates" Science, 258(5079):120-122 (1992).

Tan et al. "Monitoring the Reactions of Single Enzyme Molecules and Single Metal Ions" Analytical Chemistry, 69:4242-4248 (1997).

Zhou et al. "Universal immuno-PCR for ultra-sensitive target protein detection" Nucleic Acids Research, 21(25):6038-6039 (1993).

Extended European Search Report corresponding to European Patent Application No. 19898938.6 (12 pages) (dated Jun. 9, 2022).

Japanese Office Action corresponding to Japanese Application No. 2020-558006; mailed Jan. 9, 2024 (Foreign text 6 pages, English Translation thereof 6 pages).

* cited by examiner

Forward and reverse primers in PCR master mix.

Fig. 5

Reverse primer in PCR master mix.

Singleplex assays (chart)

Percent positive beads (y-axis, 0 to 100)

Legend:
- 90 fM IL-6
- 90 fM IL-7
- 90 fM IL-8
- 90 fM IL-10
- 815 fM TNFα
- blank x-axis categories: IL-6, IL-7, IL-8, IL-10, TNFα

1

COMPOUNDS, COMPOSITIONS, AND METHODS FOR IMPROVING ASSAYS

STATEMENT OF FEDERAL SUPPORT

This invention was made with government support under Grant No. HR011-12-2-0001 awarded by the United States Department of Defense (DARPA). The government has certain rights in the invention.

FIELD

The present invention concerns compounds, compositions, and methods for improving an assay such as, for example, a multiplexed immuno-PCR assay.

BACKGROUND

Immunoassays for target molecules such as proteins typically rely on pairs of molecular recognition elements (such as, e.g., antibodies or aptamers) to first capture and then label a target molecule so that it can be quantified. Typically, the capture antibody is bound to a solid support such as the walls of a microwell plate or the surface of microbeads. The sample is incubated with the antibody-coated surface to capture target molecules. After a wash step to remove the sample matrix, the captured target molecules are labeled with a detection recognition element (such as, antibodies or aptamers) that can be either conjugated directly to a reporter molecule (tag) or to a linking reagent (such as biotin) that allows for subsequent coupling to a tag. Alternatively, the detection recognition element can be detected with a secondary antibody that is in turn detected by means of a tag. Tags can include nanoparticles, dyes, enzymes, or nucleic acids (NAs) that can be detected by direct observation or by a chemical, or biochemical assay.

In applications that do not require high sensitivity, the tag can be a gold nanoparticle (popular in lateral flow-style assays) or a fluorescent dye that can be detected directly. One popular immunoassay that uses direct labeling has been commercialized by Lurninex Corp. In this assay, encoded microbead sets are used to perform multiplexed immunoassays. Each bead set is encoded by staining the beads with a unique combination of dyes. Each bead set is then functionalized with a different affinity reagent (e.g. antibody. antigen, etc.). The beads can be mixed together to form a multiplex bead library. During an assay, the beads are incubated with a sample to capture target molecules, if the target is present. The beads are washed and then incubated with detection antibodies that are labeled with a reporter dye or biotinylated such that they can be later labeled with a streptaviclin-conjugated reporter dye. Flow cytometry or fluorescence microscopy is used to determine both the combination of encoding dyes (to identify the bead type) and the assay signal (i.e., the signal from the reporter dye) for each bead. The concentrations of the target molecules in the sample are determined by comparing the average measured assay signal for each bead type to a standard curve. In this approach, a captured target molecule is labeled with approximately one to five, fluorophores, depending on the number of fluorophores attached to the detection antibody or its degree of biotinylation.

The enzyme linked immunosorbent assay (ELISA) is a well-known immunoassay that uses signal amplification to improve assay sensitivity. ELISA uses affinity reagent pairs to capture and label a target molecule with an enzyme, such as horseradish peroxidase, alkaline phosphatase, glueuronidase, or galactosidase. The enzyme is then used to convert a substrate into a detectable product in a concentration-dependent manner such that the concentration of the target molecule can be determined (FIG. 1). This approach is generally more sensitive than a direct labeling approach, because one enzyme label can rapidly convert many substrate molecules into detectable product molecules.

In an ELISA, capture antibody is bound to a solid phase, such as the surface of a microwell plate, and an analog signal is measured using a reader, such as a fluorescence plate reader. Multiplexing can be performed in space, where the sample is split between different wells of a microwell plate that contain different capture antibodies and to which different detection antibodies are added. Single-pot multiplexing can also be performed, but a different enzyme and substrate pair are needed for each target, adding additional complexity that is typically not practical. Alternatively, capture antibody can be linked to microbeads or magnetic microbeads for easier handling or improved workflow (FIG. 1).

In addition to ELISA, proteins and other molecules can be quantified using immuno-PCR (iPCR). The approach uses affinity reagents in a manner similar to ELISA, but unlike ELISA, the detection reagent (e.g., antibody) is labeled not with an enzyme but with a nucleic acid (NA) tag. The NA tag can be covalently linked to the antibody (forming a conjugate) or linked by an interaction such as a biotin-streptavidin bond. The tag is, usually amplified by-quantitative PCR (qPCR) to determine the concentration of the target molecule. Similar to ELISA, iPCR can be performed in an analog signal format using microwell plates coated with capture antibodies. The immuno-complex can be left intact or can be separated to release the NA tag before performing PCP. The released tag can be detected using digital PCR a droplet or microwell array format, yielding higher precision quantification. Multiplexing can be achieved by splitting the sample between singleplex reactions or by using multiple unique tag sequences with different color probe sets in a single reaction.

Similar to ELBA, iPCR, can also be performed using capture antibodies that are bound to beads (FIG. 2). Differently encoded bead sets are functionalized with separate capture antibodies so that the identity of the capture antibody bound to each bead can be decoded from the optical signal (e.g., fluorescence from different concentrations of multiple dyes attached to or embedded in the beads). Different sets of beads can, be mixed together to form bead libraries or assay panels that can quantify multiple analytes in a single sample (FIG. 3).

In a typical bead-based iPCR assay, beads are incubated with a sample to capture target molecules, washed to remove the sample matrix, and then labeled with a detection antibody (FIG. 4). If the detection antibody is covalently linked to a nucleic acid tag (i.e., a detection antibody-NA conjugate or "detection conjugate"), then the immuno-complex is complete. However, if the detection antibody is biotinylated, then the beads are incubated consecutively with streptavidin and biotinylated NA tag. Quantitative PCR is used to determine the number of NA tags and thus the original sample concentration. Multiplexed assays are more complicated than singleplex assays, because each target molecule requires a different pair of capture and detection antibodies.

Like digital ELISA described above, in a digital iPCR assay the beads are loaded into individual reaction wells to separate the PCR reactions from one another. Most wells, contain only one bead and a small amount of PCR master mix that contains primers that amplify the tag sequence. PCR amplification is performed after sealing the wells, e.g. with an immiscible oil. Bead identity is determined by examining an optical property (such as, e.g., fluorescence intensity at one or more wavelengths). PCR positive beads can be identified by several methods, such as measuring the fluorescence signal of a double-stranded DNA (dsDNA)-intercalating dye or hydrolysis probe (e.g., TaqMan probe).

At low target molecule concentrations, most beads will, have either zero or one detection conjugate, and the percentage of PCR positive beads (i.e., digital signal) can be used along with Poisson statistics to determine the average number of detection conjugates per bead and thus the concentration of the target molecules in the sample. At high target concentrations, most beads may have more than one detection conjugate, and so an analog signal (e.g. real-time PCR or another quantitative measurement of the ensemble of target molecules) can be used to determine the number of detection conjugates on each bead. Combining the digital and analog PCR signals provides a very large dynamic range (up to approximately $10^{10}$ under certain conditions) while retaining the precise quantitative ability of digital PCR at low target concentrations.

In all the immunoassays detailed above, the concentration of the detection affinity reagent (e.g., antibody) must be optimized for each target molecule. For example, if the detection antibody concentration is too low, the assay will have poor sensitivity, as the captured target molecules will not be efficiently labeled. Increasing the detection antibody concentration improves sensitivity as more captured target molecules are labeled, but this will also likely increase the background signal of the assay. An increase in background signal is often caused by nonspecific binding (TSB) of the detection reagent to the microwell or microbead surface, interaction with the capture antibody, or interactions with the bead encoding dyes in bead-based immunoassays. Unfortunately, it is impossible to distinguish positive signal that originates from a properly formed immuno-complex (FIG. 5, Complex A) from nonspecific interactions, such as inter-actions between a capture antibody and a detection antibody (FIG. 5, Complex B), the capture antibody and the NA tag (FIG. 5, Complex C), or the NA tag and the bead surface (FIG. 5, Complex D). It should be noted that the antibody portion of the detection antibody conjugate can also interact with the bead surface (FIG. 5, Complex E), and NSB can occur between detection antibodies and other proteins in the sample matrix that may have bound the beads or capture antibodies specifically or nonspecifically.

The NSB interactions described above become more severe when singleplex assays are combined into a multiplex panel, often requiring re-optimization of detection antibody concentrations and other assay parameters. The primary reason NSB increases in multiplex assays is that as more target molecules are added to the assay, the total detection antibody concentration increases, which typically increases the signal observed from NSB. Additionally, cross-reactivity between antibodies and off-target molecules can become a larger issue in a multiplex assay format. There are multiple forms of cross-reactivity that can affect assay signal. For example, an antigen can bind a wrong (off-target) capture antibody and then be detected, by its own detection antibody, which would result in false-positive signal. In a similar example, an antigen can bind a Wrong (off-target) capture antibody but is not detected by a detection antibody. In this instance, the incorrectly-captured antigen can block (i.e., competitively inhibit) binding and subsequent detection of the real target, resulting in a false-negative signal.

Although signal due to cross-reactivity and NSB can sometimes be mitigated for lower sensitivity, direct-label assays or for bulk, analog assays, it is a much more significant problem for single molecule assays, because even a single NSB event per bead can be deleterious to digital assay performance. High-sensitivity, multiplex assays are typically limited to about 5-10 different targets, because NSB and cross-reactivity between detection chemistries significantly reduces signal to noise and raises limits of detection.

In addition to the issues highlighted above, multiplexed PCR often suffers from off sequence amplification and competition between primer and probe sets. In order to realize highly sensitive iPCR assays at higher levels of multiplexing, another approach is needed,

SUMMARY

Aspects of the present invention are directed to compounds, compositions, kits, systems, devices, and methods for improving an assay such as, for example, a multiplexed PCR assay (e.g., a multiplexed immuno-PCR assay).

One aspect of the present invention is directed to a kit comprising: (i) a solid support (e.g., a bead), wherein the solid support comprises: an encoding agent (e.g., a dye); a first nucleic acid sequence (e.g., an oligonucleotide and/or primer); and a first molecular recognition element (e.g., an antibody); and (ii) a detection reagent comprising a second molecular recognition element (e.g., an antibody) and a second nucleic acid sequence, wherein at least a portion of the first nucleic acid sequence and at least a portion of the second nucleic acid sequence are configured to participate in a nucleic acid amplification process. In some embodiments, the solid support and the detection reagent are separately stored. In some embodiments, the solid support and the detection reagent are present in the same composition and/or are stored and/or provided together.

Another aspect of the present invention is directed to a solid support (e.g., a bead) comprising: an encoding agent (e.g., a dye); a nucleic acid sequence; and a molecular recognition element (e.g., an antibody).

A further aspect of the present invention is directed to a plurality of solid supports comprising: (i) a first plurality of solid supports and each solid support in the first plurality of solid supports comprises: a first encoding agent (e.g., a dye) that provides a first encoding signal; a first nucleic acid sequence; and a first molecular recognition element (e.g., an antibody); and (ii) a second plurality of solid supports and each solid support in the second plurality of solid supports comprises: a second encoding agent (e.g., a dye) that provides a second encoding signal; a second nucleic acid sequence; and a second molecular recognition element (e.g., an antibody), wherein the first encoding signal is different than the second encoding signal, the first nucleic acid sequence is different than the second nucleic acid sequence, and the first molecular recognition element is different than, the second molecular recognition element.

Another aspect of the present invention is directed to a plurality of detection reagents comprising: (i) a first plurality of detection reagents and each detection reagent in the first plurality of detection reagents comprises a first molecular recognition element (e.g., an antibody) and a first nucleic acid, sequence; and (ii) a second plurality of detection reagents and each detection reagent in the second plurality of detection reagents comprises a second molecular recognition element (e.g., an antibody) and a second nucleic acid sequence; wherein the first and second nucleic acid sequences each include a first portion and a second portion; and wherein the nucleic acid sequence of the first portion for the first nucleic acid sequence is different than the nucleic acid sequence of the first portion for the second nucleic acid sequence. In some embodiments, the nucleic acid sequences of the second portion for the first and second nucleic acid sequences are the same.

A further aspect of the present invention is directed to a method of detecting a target in a sample, the method comprising: combining a solid support as described herein and a sample comprising the target to form a first composition comprising a target bound solid support; optionally washing the target bound solid support (e.g., with an aqueous solution); combining a detection reagent and the target bound solid support to form a complex comprising the solid support, target, and detection reagent, wherein the detection reagent comprises a second molecular recognition element and a second nucleic acid sequence and at least a portion of the first nucleic acid sequence and at least a portion of the second nucleic acid sequence are configured to participate in a nucleic acid amplification process; optionally washing the complex (e.g., with an aqueous solution); optionally combining an amplification agent (e.g., a reverse primer, a ssDNA splint and ligase, etc.) and the complex; optionally releasing a nucleic acid sequence from the solid support; and amplifying at least a section of the second nucleic acid sequence, thereby detecting the target in the sample.

Another aspect of the present invention is directed to a method of improving the specificity and/or reducing the background signal for an assay, the method comprising: providing a solid support as described herein or a plurality of solid supports as described herein; and performing the assay in the presence of the solid support or the plurality of solid supports, thereby improving the specificity and/or reducing the background signal for an assay.

It is noted that aspects of the invention described with respect to one embodiment, may be incorporated in a different embodiment although not specifically described relative thereto. That is, all embodiments and/or features of any embodiment can be combined in any way and/or combination, Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred, embodiments that follow, such description being merely illustrative of the present invention.

BRIEF DESCRIPTION OF THE DRAWINGS

FIG. 5 is a schematic illustration of interactions that can provide a true positive or false positives in an immunoassay.

6

Figure 6:
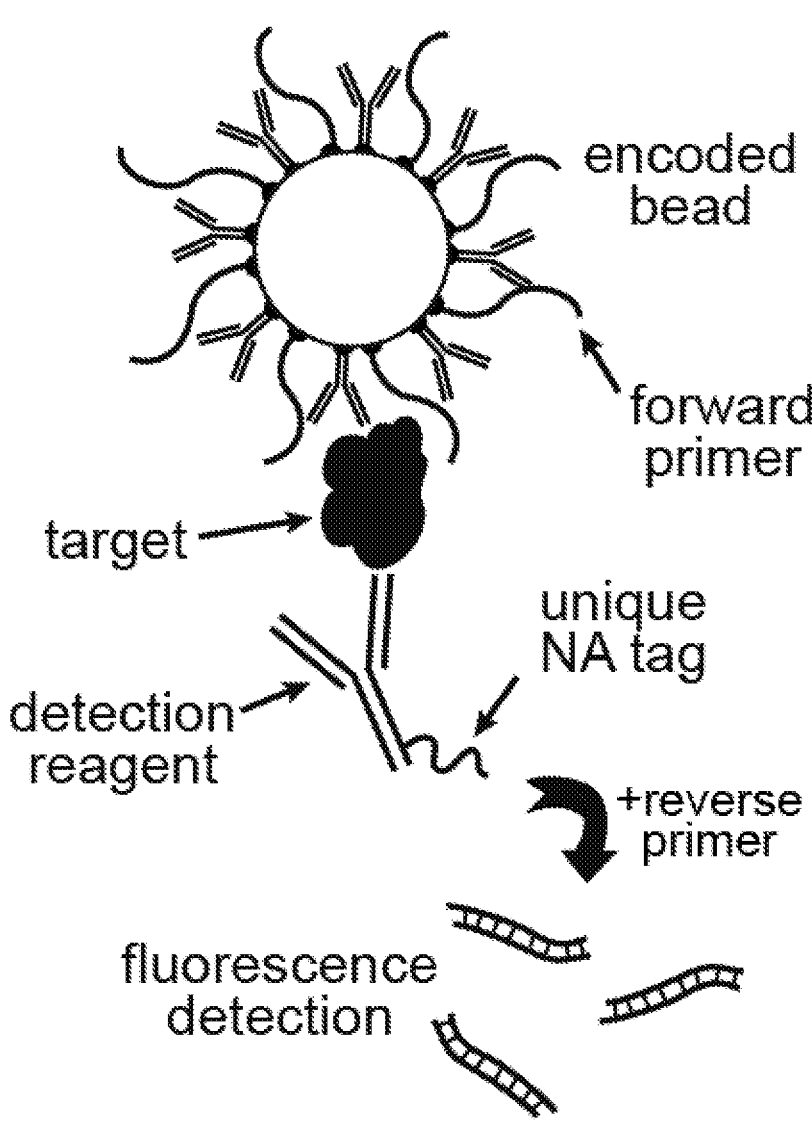

FIG. 6 is a schematic illustration of an example complex formed according to some embodiments of the present invention.

Figure 7:
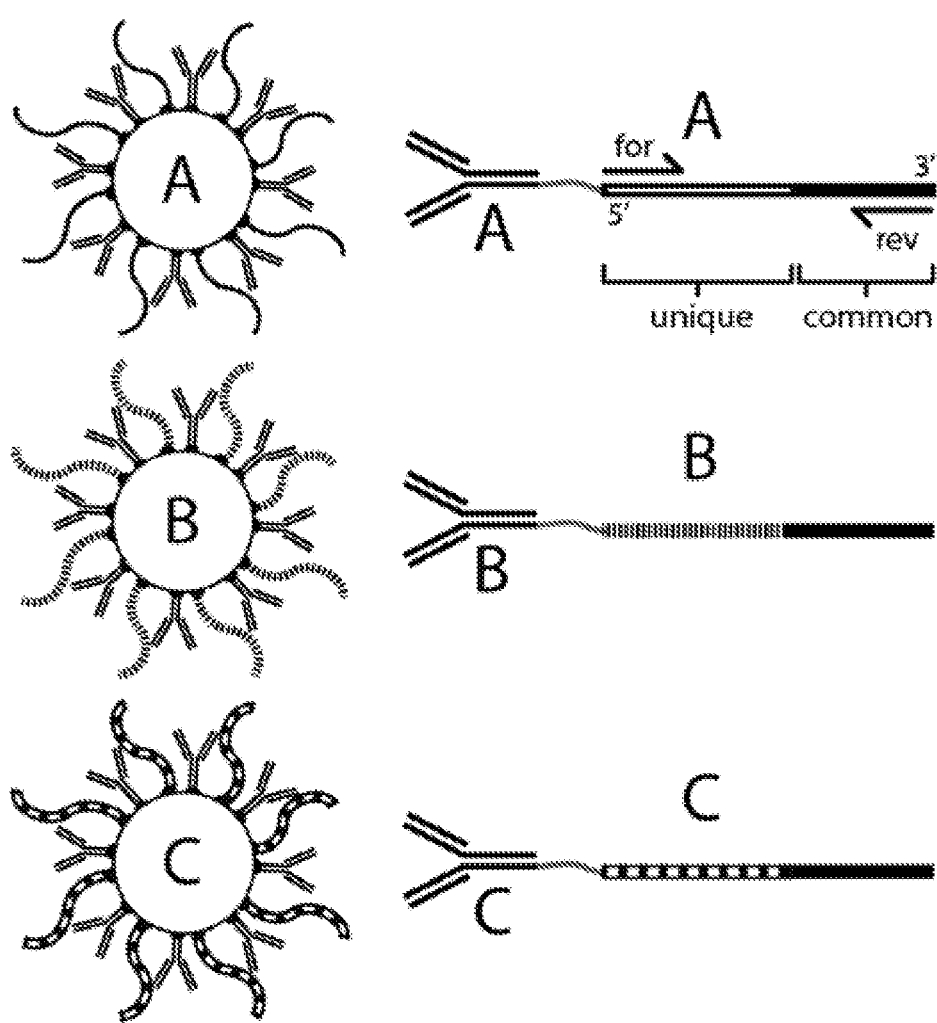

FIG. 7 is a schematic illustration of bead sets prepared by encoding each set with a unique dye or combination of dyes and the corresponding detection reagent for each set includes a different nucleic acid tag according to some embodiments of the present invention.

Figure 8:
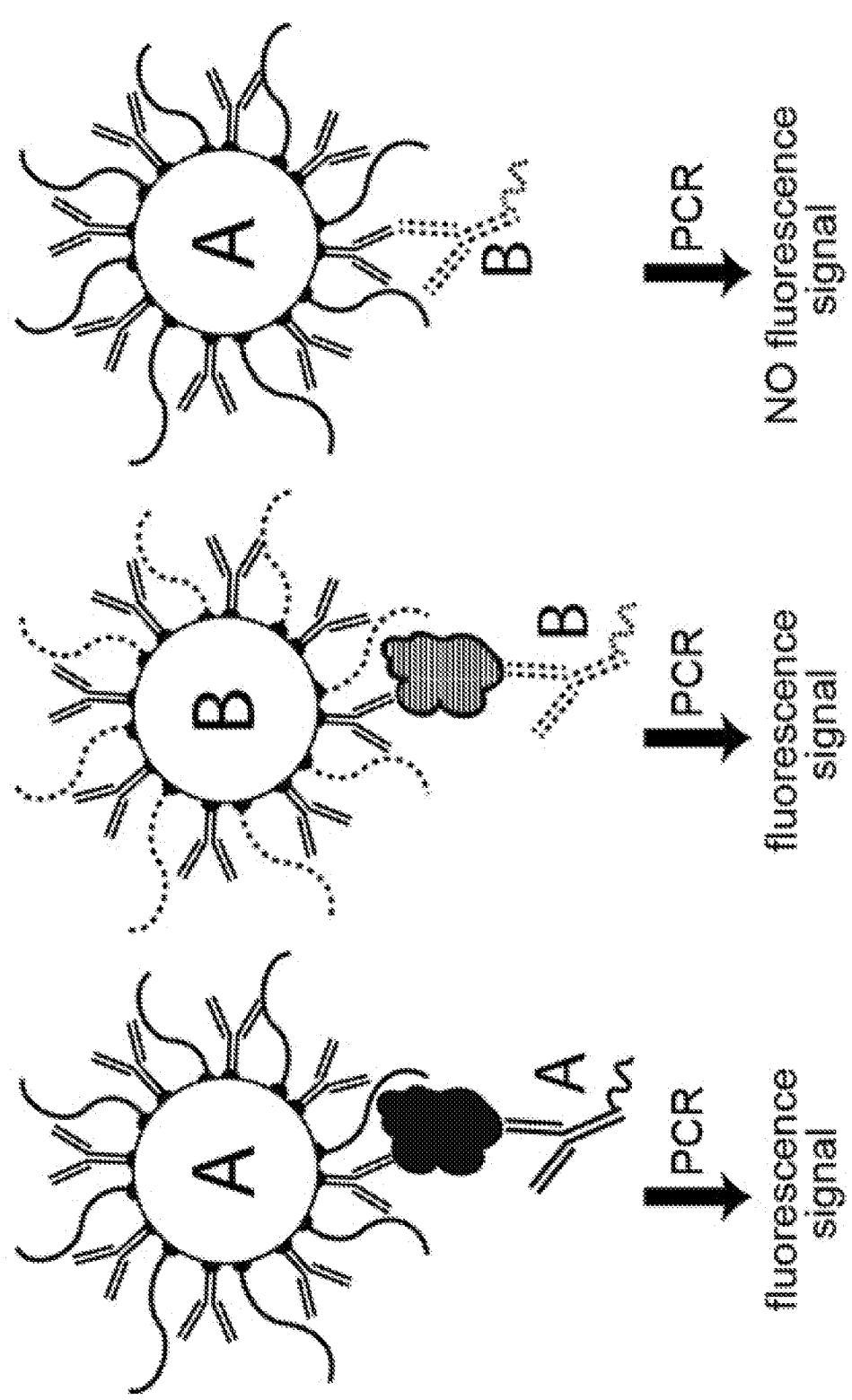

FIG. 8 is a schematic illustration of example complexes correctly formed (i.e., the capture antibodies on the bead bind to the appropriate target and the corresponding detection reagent is also bound to the target) according to some embodiments of the present invention, which results in fluorescence signal, and a complex incorrectly formed (i.e. the capture antibodies on the bead bind to a detection reagent that is not the bead's corresponding detection reagent) and does not produce a fluorescence signal.

Figure 9A:

FIG. 9A is a graph showing the percentage of positive beads provided in singleplex assays for different targets.

Figure 9B:

FIG. 9B is a graph showing the percentage of positive beads provided in a multiplex assay for different targets.

Figure 9C:
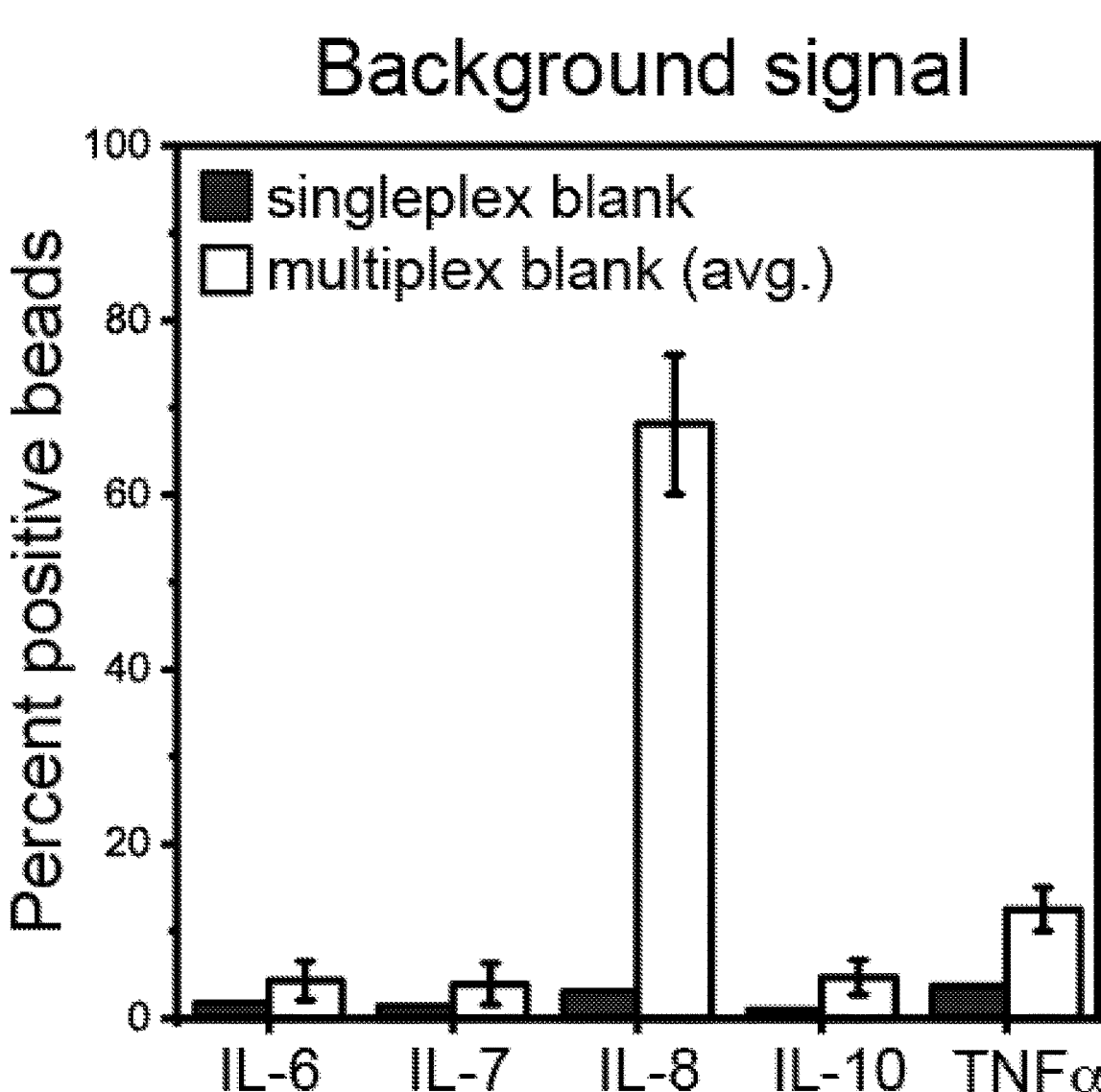

FIG. 9C is a graph showing the background signal for the singleplex assays and multiplex assay referenced in FIGS. 9A and 9B, respectively.

Figure 10:
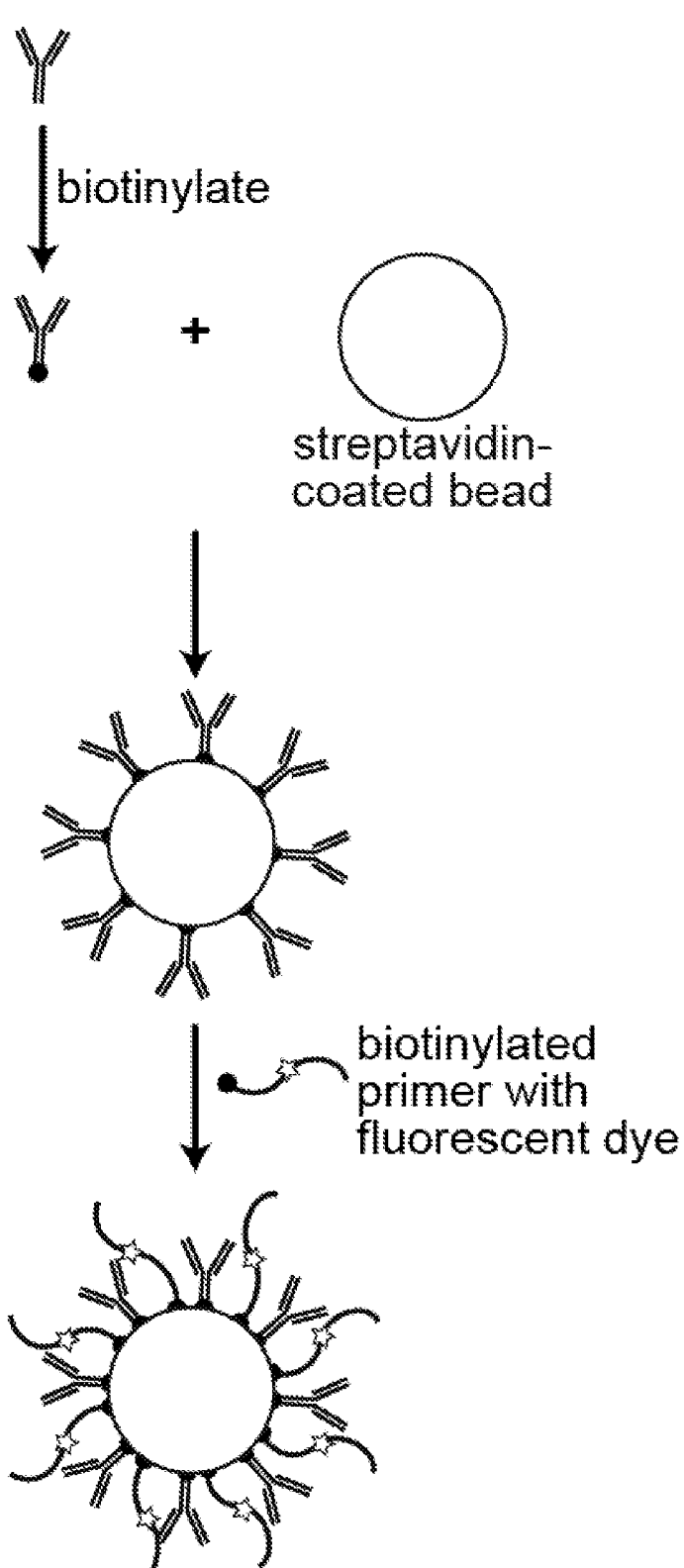

FIG. 10 is a schematic illustration of a method of preparing a solid support according to some embodiments of the present invention.

Figure 11:
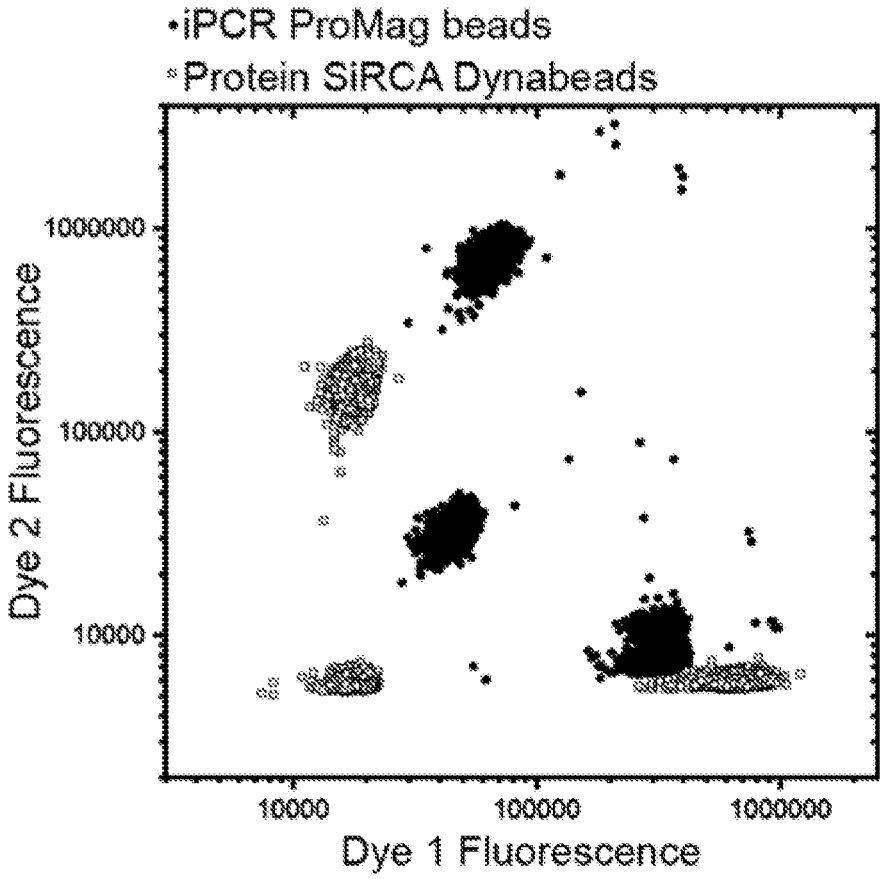

FIG. 11 is a plot of fluorescence intensity of encoding dyes bound to representative beads from different bead sets.

Figure 12:
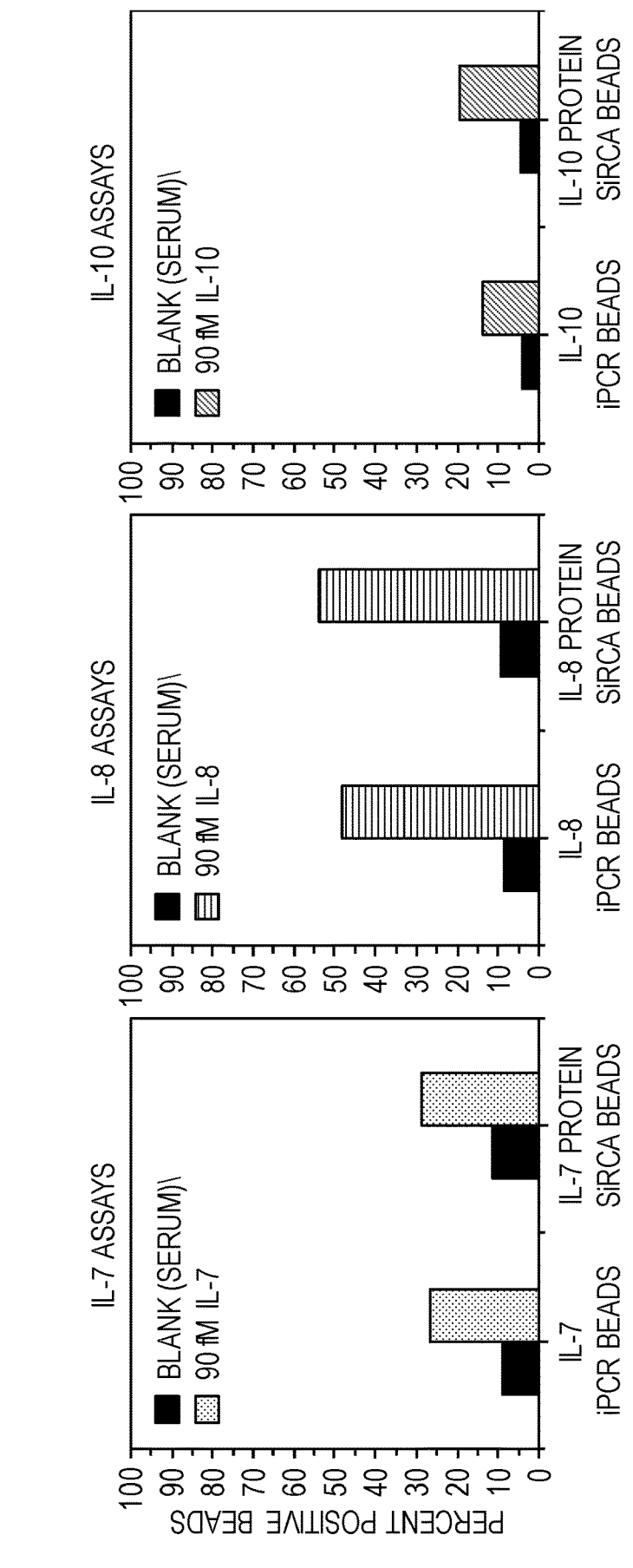

FIG. 12 provides graphs comparing the percentage of positive beads of conventional iPCR beads to the percentage of positive beads prepared according to some embodiments of the present invention. iPCR dAb conjugates were used for all assays with 1 set of primers included in the PCR master mix.

Figure 13:
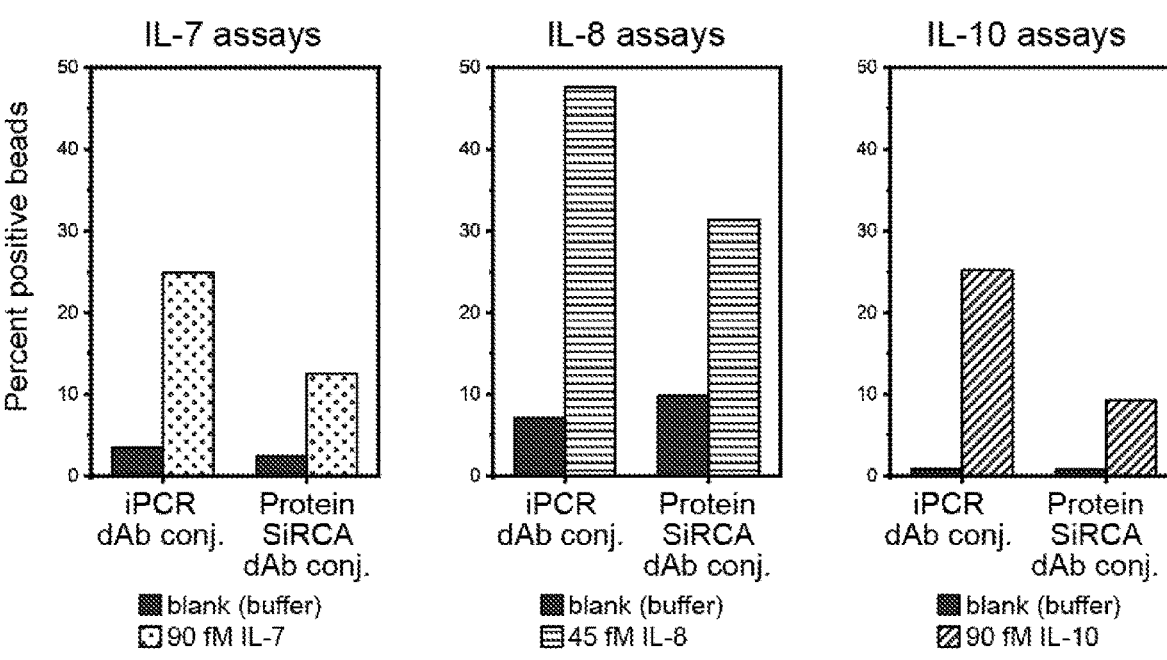

FIG. 13 provides graphs comparing the activity of conventional iPCR detection reagent conjugates to the activity of detection reagents prepared according to some embodiments of the present invention. iPCR beads were used for all assays with 1 set of primers included in the PCR master mix.

Figure 14:
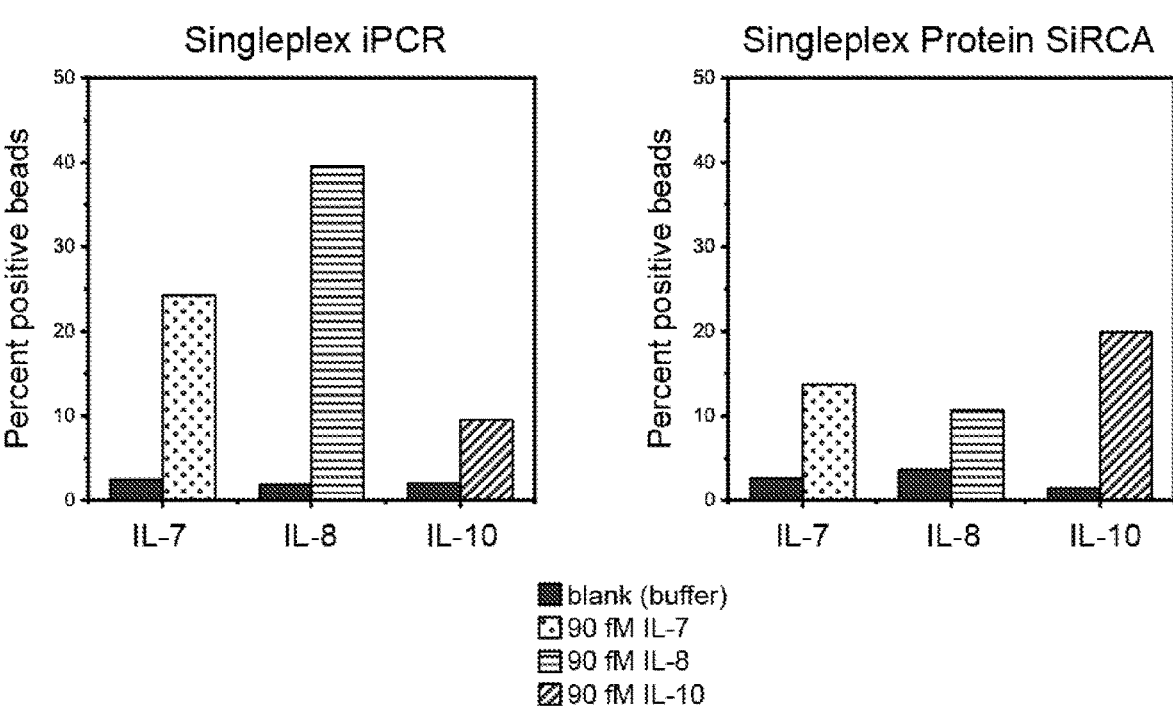

FIG. 14 provides graphs comparing the percentage of positive beads for various targets in a baseline singleplex assay using a conventional iPCR system to the percentage of positive beads for the same targets using a system according to some embodiments of the present invention.

Figure 15:
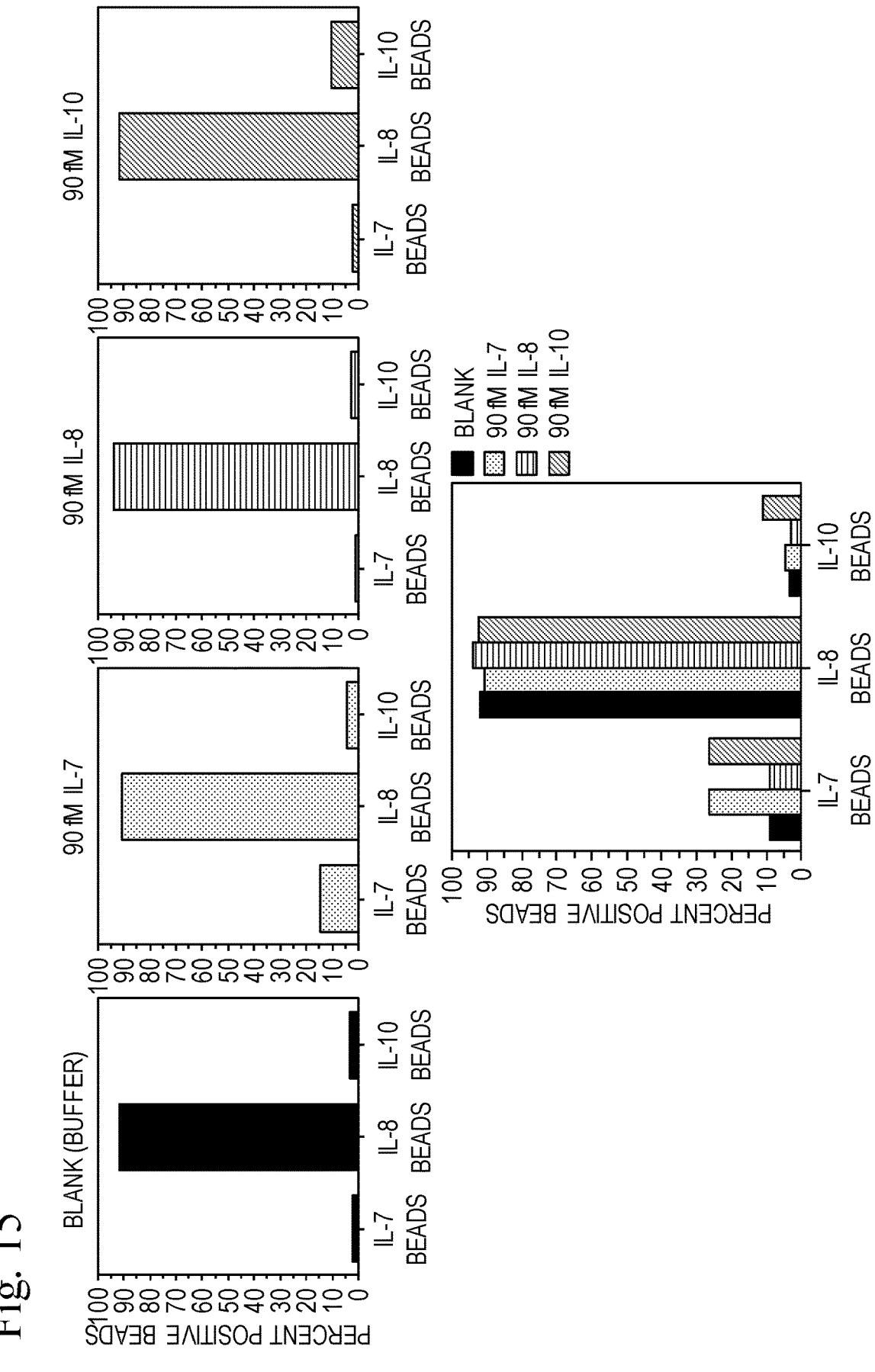
Figure 16:
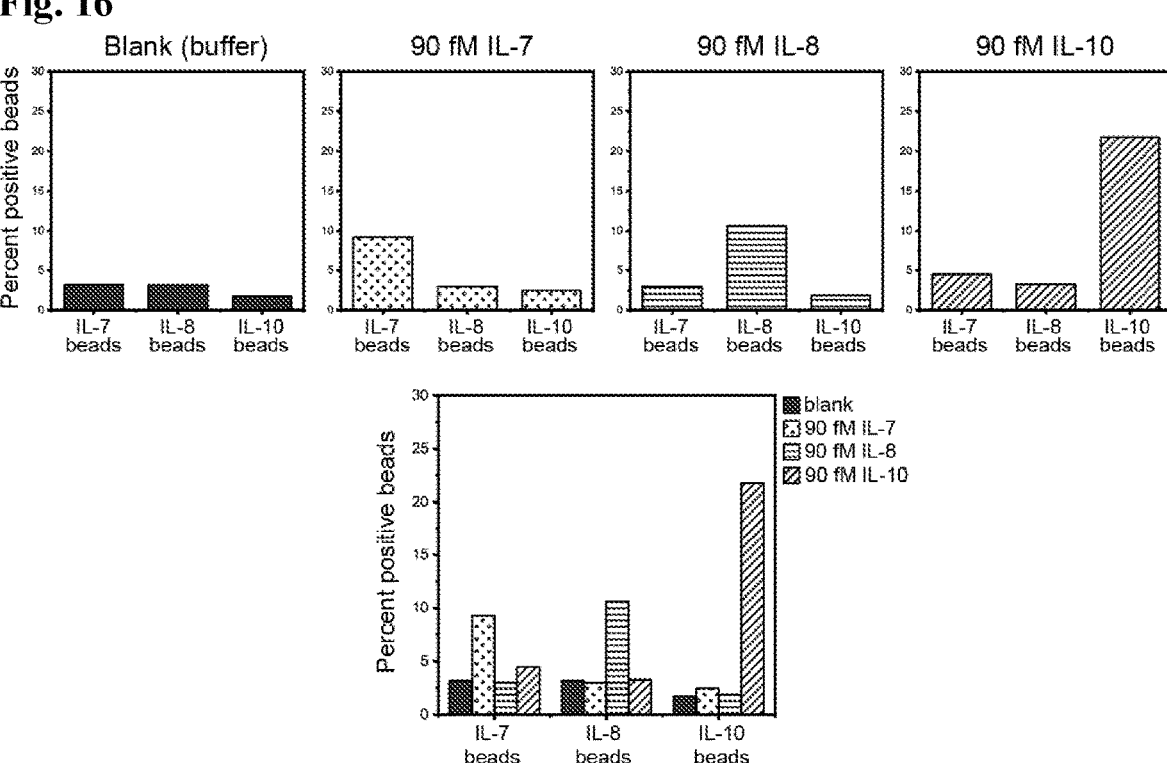

FIG. 15 provides graphs showing the signal achieved for each bead type in the three-plex iPCR, assay and a graph comparing the different assay conditions, FIG. 16 provides graphs showing the signal achieved for each bead type in the three-plex assay according to some embodiments of the present invention and a graph comparing the different assay conditions.

Figure 17:
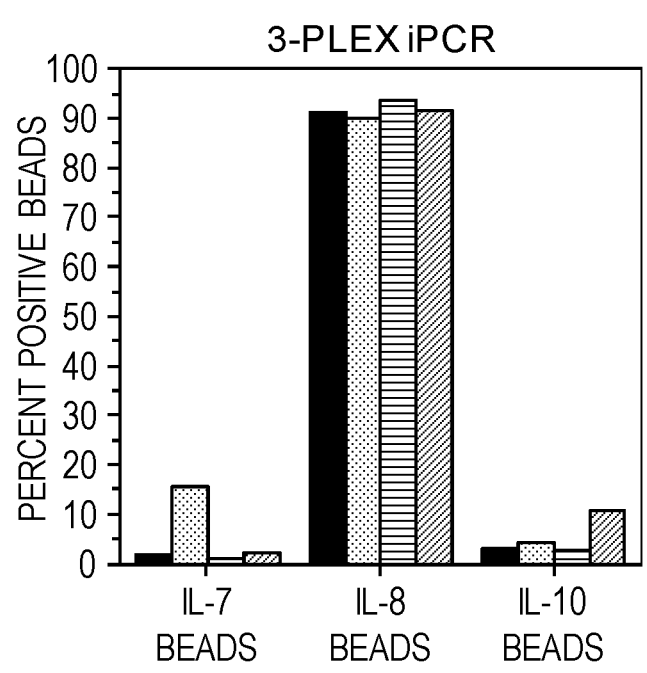
Figure 17:
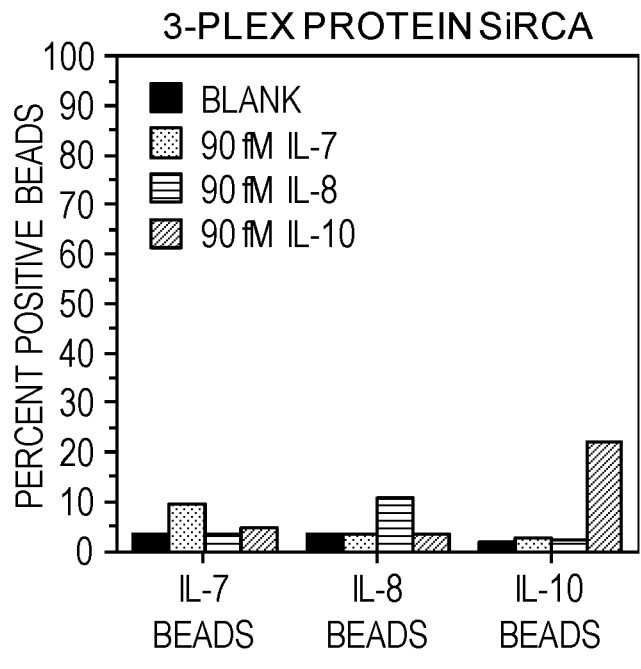

FIG. 17 provides the comparison graph for the three-plex iPCR assay of FIG. 15 and the comparison graph for the three-plex assay according to some embodiments of the present invention of FIG. 16.

DETAILED DESCRIPTION OF EXAMPLE EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention, As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted, as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

It will also be understood that, as used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

The term "about," as used herein when referring to a measurable value such as an amount or concentration and the like, is meant to encompass variations of ±20%, ±10%, ±5%, ±1%, ±0.5%, or even ±0.1% of the specified value as well as the specified value. For example, "about X" where X is the measurable value, is meant to include X as well as variations of ±20%, ±10%, ±5%, ±1%, ±0.5%, or even ±0.1% of X. A range provided herein for a measurable value may include any other range and/or individual value therein.

As used herein, the terms "increase," "increases," "increased," "increasing," "enhance," and similar terms indicate an elevation in the specified parameter of at least about 2%, 5%, 10%, 15%. 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 2%, 5%, 10%, 15%, 20%, 25%, 30%, 35%, 40%, 45%, 50%, 55%, 60%, 65%, 70%, 75%, 80%, 85%, 90%, 95%, 97%, or 100%.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under," The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second." etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the terms "nucleic acid," "nucleic acid molecule," "nucleotide sequence," "nucleic acid sequence," "oligonueleotide," and "polynucleotide" refer to RNA or DNA that is linear or branched, single or double stranded, or a hybrid thereof. The terms also encompass RNA/DNA hybrids. In some embodiments, the RNA and/or DNA can include a chemically modified base such as, for example, those that are not usually found in nature, and the chemically modified base may improve the specificity of an assay (e.g., a PCR reaction) and/or reduce nonspecific binding between other RNA and/or DNA. When dsRNA is produced synthetically, less common bases, such as inosine, 5-methylcytosine, 6-methyladenine, hypoxanthine and others may be used for antisense, dsRNA, and ribozyme pairing. For example, poly-nucleotides that contain C-5 propyne analogues of uridine and cytidine have been shown to bind RNA with high affinity and to be potent antisense inhibitors of gene expression. Other modifications, such as modification to the phosphodiester backbone, or the 2' hydroxy in the ribose sugar group of the RNA can also be made.

As used herein, the terms "nucleotide sequence" and "nucleic acid sequence" are used interchangeably and refer to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense MA, any of which can be single stranded and/or double stranded. The terms "nucleotide sequence," "nucleic acid." "nucleic acid molecule," "oligonucleotide" and "polynueleotide" are also used interchangeably herein to refer to a heteropolymer of nucleotides. Nucleic acid molecules and/or nucleotide sequences provided herein are presented in the 5' to 3' direction, from left to right and are represented using the standard code for representing the nucleotide characters as set forth in the U.S. sequence rules, 37 CFR. §§ 1.821-1.825 and the World Intellectual Property Organization (WIPO) Standard ST.25, A "5' region" as used herein refers to the region of a polynucleotide that is nearest the 5' end. Thus, for example, an element in the 5' region of a polynucleotide can be located anywhere from the first nucleotide located at the 5' end of the polynucleotide to the nucleotide located halfway through the polynueleotidc. A "3' region" as used, herein refers to the region of a polynucle-otide that is nearest the 3' end. Thus, for example, an element in the 3' region of a polynucleotide can be located anywhere from the first nucleotide located at the 3' end of the poly-nucleotide to the nucleotide located halfway through the polynueleotide.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Comple-mentarity between two single-stranded molecules may be "partial," in which only some of the nucleotides bind, or it may be complete when total complementarity exists between the single stranded molecules. The degree of complementarity between nucleic acid strands has signifi-cant effects on the efficiency and strength of hybridization between nucleic acid strands.

"Complement" as used herein can mean 100% comple-mentarity with the comparator nucleotide sequence or it can mean less than 100% complementarily (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "section" of a nucleic acid sequence of the present invention will be understood to mean a nucleic acid sequence of reduced length relative (e.g., reduced by 1, 2, 3, 4, 5, , 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, or more nucleotides) to a reference nucleic acid sequence and that comprises a nucleic acid sequence of contiguous nucleotides identical or almost iden-tical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid sequence. Such a nucleic acid portion according to the present inven-tion may be, where appropriate, included in any part of larger polynucleotide of which it is a constituent.

A "fragment" of an amino acid sequence of the present invention will be understood to mean an amino acid sequence of reduced length relative (e.g., reduced by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, or more amino acids) to a reference amino acid sequence and that comprises an amino acid sequence of contiguous amino acids identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference amino acid sequence. Such an amino acid fragment according to the present invention may be, where appropriate, included in a larger protein or peptide of which it is a constituent.

As used herein "sequence identity" refers to the extent to which two optimally aligned polynucleotide or peptide sequences are invariant throughout a window of alignment of components, e.g., nucleotides or amino acids, "Identity" can be readily calculated by known methods including, but not, limited to, those described in: Computational Molecular Biology (Lesk, A. M., ed.) Oxford University Press, New York (1988); Biocomputing: Informatics and Genome Proj-ects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a refer-ence ("query") polynucleotide molecule (or its complemen-tary strand) as compared to a test ("subject") polynucleotide molecule (or its complementary strand) when the two sequences, are optimally aligned. In some embodiments, "percent, identity" can refer to the percentage of identical amino acids in an amino acid sequence.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%. 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence compari-son algorithms or by visual inspection. In some embodi-ments of the present invention, the substantial identity exists over a region of consecutive nucleotides of a nucleotide sequence of the invention that is about 4 nucleotides to about 30 nucleotides, about 5 nucleotides to about 20 nucleotides, about 16 nucleotides to about 30 nucleotides, about 18 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleo-tide sequences can be substantially identical over at least about 5, 10, 15, 20, or 25 consecutive nucleotides. In some embodiments, the nucleotide sequences can be substantially identical over at least about 5 consecutive nucleotides. In some embodiments, a substantially identical nucleotide or protein sequence performs substantially the same function as the nucleotide or protein sequence to which it is substan-tially identical.

For sequence comparison, typically one sequence acts as a reference sequence to which test sequences are compared.

When using a sequence comparison algorithm, test and reference sequences are entered into a computer, subsequence coordinates are designated if necessary. and sequence algorithm program parameters are designated. The sequence comparison algorithm then calculates the percent sequence identity for the test sequence(s) relative to the reference sequence. based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Packages® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence, or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen Laboratory Techniques in Biochemistry and Molecular Biology-Hybridization with Nucleic Acid Probes part 1 chapter 2 "Overview of principles of hybridization and the strategy of nucleic acid probe assays" Elsevier, New York (1993). Generally, highly stringent hybridization and wash conditions are selected to be about 5° C. lower than the thermal melting point (Tm) for the specific sequence at a defined ionic strength and pH.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2× saline-sodium citrate (SSC) wash at 65° C. for 15 minutes (see, Sambrook, infa, for a description of SSC buffer). Often, a high stringency wash is preceded by a low stringency wash to remove background probe signal. An example of a medium stringency wash for a duplex of, e.g., more than 100 nucleotides, is 1× SSC at 45° C. for 15 minutes. An example of a low stringency wash for a duplex of, e.g., more than 100 nucleotides, is 4-6× SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO4, 1 mM EDTA at 50° C. with washing in 2× SSC, 0.1% SDS at 50° C. In another embodiment, the reference, nucleotide sequence hybridizes to the "test" nucleotide sequence in 7% sodium dodecyl sulfate (SDS), 0.5 M NaPO4, 1 mM EDTA at 50° C. with washing in 1× SSC, 0.1% SDS at 50° C. or in 7% sodium dodecyl sulfate (SDS), 0.5 M NaPO4, 1 mM EDTA at 50° C. with washing in 0.5° SSC, 0.1% SDS at 50° C. In still further embodiments, the reference nucleotide sequence hybridizes to the "test" nucleotide sequence in 7% sodium dodecyl sulfate (SDS), 0.5 M NaPO4, 1 mM EDTA at 50° C. with washing in 0.1× SSC, 0.1% SDS at 50° C., or in 7% sodium dodecyl sulfate (SDS), 0.5 M NaPO4, 1 mM EDTA at 50° C. with washing in 0.1× SSC, 0.1% SDS at 65° C.

The term "target" as used herein refers to any analyte of interest that may be present in a sample. Example targets include, but are not limited to, synthetic or natural chemical and/or biological macromolecules, nanoparticles, small molecule compounds, DNA, nucleic acids/polynucleic acids, peptides, proteins and/or the like. The target may be one or more analyte molecules. In some embodiments, a target may be present in a sample, optionally wherein the sample is obtained from a source (e.g., a subject, water supply, food supply, etc.). A target and/or sample may include one or more polar metabolites such as, e.g., amino acids and/or charged molecules, peptides, and/or proteins. A target and/or sample may include one or more chemical and/or biological compound(s) extracted from a biofluid, tissue, blood, serum, urine, cell growth media, lysed cells, beverage, and/or food, etc. In some embodiments, a target may be from and/or present in an environmental sample such as, for example, a water, air and/or soil sample. In some embodiments, a target may be from and/or present in a forensic sample. In some embodiments, a target and/or sample may include a pooled sample comprising a mixture of two or more samples.

As used herein, "contact", "contacting", "contacted," and grammatical variations thereof, refer to placing two or more components together or in sufficient proximity such that, under suitable conditions, a desired reaction can be carried out (e.g., binding, transcriptional control, genome editing, nicking, cleavage, and/or amplifying nucleic acids).

Embodiments of the present invention can address and/or reduce one or more problem(s) in an assay (e.g., a multiplexed iPCR assay) such as, for example, background signal problems such as, e.g., those caused by nonspecific binding (NSB) and/or antibody cross-reactivity problems. Embodiments of the present invention may comprise and/or utilize a combination of unique nucleic acid tags and provide a solid support (e.g., bead) based delivery to form spatially multiplexed PCR reactions, which may avoid the common complications associated with single-reaction, multiplexed PCR.

According to some embodiments of the present invention a solid support is provided. The term "solid support" as used herein includes one or more of an object such as, e.g., a microbead, chip, plate, slide, pin, plate well, bead, microsphere, nanoparticle, microwell or other member that may be used to provide a nucleic acid sequence and molecular recognition element and/or that may be coupled to or labeled with an encoding agent (such as, e.g., a fluorescent compound, a chemiluminescent compound, a radioactive element, and/or an enzyme) and/or a dynamic element. A nucleic acid sequence, molecular recognition element, encoding agent and/or a dynamic element may be directly Or indirectly attached to or embedded (partially or fully) within a solid support, such as, for example, by covalent attachment, noncovalent attachment, and/or physical incorporation. In some embodiments, a solid support may be a printed array on a solid surface. In some embodiments, a solid support may be a microsphere. In some embodiments, a solid support may be a solid surface on which a sample, such as, e.g., a chemical and/or biological component (e.g., a tissue sample), is contacted and a molecular recognition element on the solid support (optionally comprising one or more encoding agent(s)) may attach to a portion of the sample and/or a target therein. The molecular recognition element may comprise or may be an antibody or fragment thereof, aptamer, DNA hybridization probe, oligonucleotide, peptide, protein, and/or combinations thereof. In some embodiments, a solid support may comprise a labile reagent and/or support bond, each of which may allow for cleavage of a component (e.g., a nucleic acid sequence) from the solid support.

In some embodiments, one or more encoding agents may be attached to a solid support (e.g., a bead or microsphere) to provide an encoded solid support (e.g., an encoded bead or encoded microsphere). In some embodiments, one or more encoding agents may be attached to a molecular recognition element (e.g., an antibody) to provide an encoded molecular recognition element (e.g., an encoded antibody), which may be attached to the solid support and thereby provide an encoded solid support. In some embodiments, an encoded molecular recognition element may be attached to a particle, such as, for example, a nanoparticle. In some embodiments, methods of the present invention may include providing or binding one or more encoding agents and/or encoded molecular recognition elements onto a solid support. In some embodiments, a solid support and/or encoded solid support is one as described in International Publication No. WO 2017/112025, the contents of which are incorporated herein by reference in its entirety.

The term "bead" or "beads" as used herein refers to a solid phase member such as, for example, particles, granules or microspheres, typically magnetic microspheres, that can be porous, superficially porous, or nonporous material(s) such as, e.g., polymers, plastics, glass, silicon dioxide, metal or semimetal oxides (including but not limited to aluminum oxides, titanium oxides, zirconium oxides or other oxides), quantum dots, metal particles, and/or the like, which may be appropriate for use in reaction wells, in some embodiments, a multiplexing bead set may be provided comprising a plurality of beads (e.g., microspheres) that are uniquely encoded to distinguish one population of beads from another.

In some embodiments, the solid support is a bead such as, for example, a magnetic or superparamagnetic bead. In some embodiments, the solid support is not a magnetic or superparamagnetic bead. In some embodiments, the solid support is a bead that is porous and/or that has a coating that increases its surface area. In some embodiments, the solid support is a bead that is made by creating aggregates of microparticles and/or nanoparticles, optionally with some or all of the microparticles and/or nanoparticles functionalized so that they may be used to carry reagents such as, e.g., capture affinity reagents, primers, probes, blocking agents, polymerase, reverse transcriptase, and/or other enzymes.

In some embodiments, a solid support (e.g., a bead) comprises an encoding agent (e.g., a dye), a nucleic acid sequence, and a molecular recognition element (e.g., an antibody). In some embodiments, the encoding agent is attached to or at least partially embedded within the solid support directly or indirectly. In some embodiments, the nucleic acid sequence and/or molecular recognition element of the solid support comprises the encoding agent. The molecular recognition element may comprise or may be an antibody or a fragment thereof, aptamer, modified aptamer, DNA hybridization probe, oligonucleotide, peptide, protein, carbohydrate, and/or combinations thereof.

The term "encoding agent" as used herein refers to one or more agents (e.g., chemicals, proteins, etc.) associated with (e.g., applied to, attached to, bound to, compounded with, used to fabricate or create, etc.) a solid support and/or a material of the solid support and/or a material in contact with the solid support that provides and/or will generate an encoding signal for the respective solid support (which may be all or a portion thereof). In some embodiments, one or more encoding agents provide and/or generate a detectable encoding signal that allows for differentiation of a solid support (e.g., bead) population or sub-population. For example, in some embodiments, one or more encoding agents may provide and/or generate a detectable encoding signal for an individual solid support (e.g., a bead) to which the one or more encoding agents are associated (e.g., attached) and/or one or more encoding agents may provide and/or generate a detectable encoding signal for a particular portion of a solid support to which the one or more encoding agents are attached (e.g., the portion of the solid support to which a molecular recognition element comprising the one or more encoding agents binds).

An encoding signal may be provided and/or generated by one or more encoding agents associated with a solid support and/or by the solid support itself and/or a material (e.g., compound) associated with the solid support. In some embodiments, the encoding signal may be the size and/or shape of the solid support. In some embodiments, the encoding signal is a signal (e.g., an optical and/or electrical signal) that is generated by one or more encoding agents (e.g., chemicals, proteins, etc.) associated with (e.g., applied to, attached to, bound to, compounded with, used to fabricate or create, etc.) a solid support and/or by the solid support. A detectable encoding signal may be optically and/or electronically detectable, which may be perceived visually with the human eye and/or electronically read, detected, and/or obtained. The detectable encoding, signal can comprise intensity, typically at or above a defined threshold value, a color (e.g., color hue, color intensity, and/or color value), a color and intensity, and/or a change in size, shape, and/or radioactivity. In some embodiments, the detectable encoding signal comprises a luminescence intensity, which may include a fluorescence, phosphorescence, and/or chemiluminescence intensity.

The encoding, signal for a respective solid support (which may be all or a portion thereof) may be detectable (e.g., detectable optically, electronically, electrochemically, electrostatically, magnetically, etc.) or may not, be detectable. In some embodiments, the encoding signal for a respective solid support (which may be all or a portion thereof) may change. For example, the encoding signal for a respective solid support may change from detectable to not detectable, from not detectable to detectable, from a greater value to a lower value (e.g., from a greater signal amplitude, fluorescence intensity value, diameter, etc.), and/or from a lower value to a greater value. The change in an encoding signal for a respective solid support may occur over time and/or may occur due to at least one chemical and/or physical change associated with the solid support. In some embodiments, an encoding signal for a solid substrate may change and/or may be provided and/or generated by a change in the environment in which the solid support is present (e.g., a change in a solution in which the solid support and/or encoding agent is in contact with). For example, an encoding signal for, a solid support may change and/or may be provided and/or generated by a change in magnetic behavior, pH, light scattering, physical size (increase or decrease), shape, refractive index, solubility, light absorbance and/or emission intensity or maxima wavelengths shifts, conductivity, dielectric constant, viscosity, and radio emission from isotopic decay, and combinations of the above.

The term "decoding" refers to (typically electronic/programmatic) identification of different populations of a respective sample (including, e.g., a sample of solid supports and/or a sample comprising a plurality of encoded molecular recognition elements) based at least in part on the encoding signal from encoded solid support(s) and/or encoded molecular recognition elements. Detection and/or identification of one or more encoding signals can allow for the decoding, of the sample to determine the identity of the particular solid support population and/or to detect a target.

A "dynamic element" as used herein refers to a chemical and/or biological compound that provides or exhibits a physical and/or chemical change in response to a Defined Event. The physical and/or chemical change may modify the encoding signal for a respective solid support (which may be all or a portion thereof) at a point in time compared to the encoding signal at a different (e.g., earlier) point in time and may be detectable (e.g., optically and/or electrically detectable). A "dynamic element" may include an encoding agent a dye, protein, etc.) and/or a solid support (e.g., a microsphere). The physical and/or chemical change may be a physical and/or chemical change that affects a solid support (e.g., the change may be, a change in the charge and/or color of a solid support and/or may be a change in the size and/or shape of a solid support). Thus, the dynamic element may be the solid support and/or a compound attached and/or associated with the solid support. In some embodiments, the physical and/or chemical change is a physical and/or chemical change that affects an encoding agent associated with the solid support (e.g., the change may be in the stability of a linker binding the encoding agent to the solid support, the solvent accessibility of an encoding agent, and/or the presence and/or absence of a quencher). Thus, the dynamic element may be the encoding agent and/or a compound attached to and/or associated with the encoding agent (e.g., a quencher). The physical and/or chemical change may be reversible or irreversible. In some embodiments, the dynamic element may be an encoding agent. In some embodiments, a dynamic element and/or encoding agent is one as described in International Publication No. WO 2017/112025, the contents of which are incorporated herein by reference is its entirety.

Encoding of solid supports can be achieved by any method known to those in the art (e.g., using color, fluorescence color, size, shape, a property that changes such as a thermally-labile or photo-labile dye, and/or any combination thereof), In some embodiments, a solid, support may comprise an encoding, agent that is covalently or noncovalently attached to the solid support. In some embodiments, a dye is embedded in the solid support (e.g., bead) such as, e.g., via solvent-swelling and entrapment.

In some embodiments, the solid support comprises one or more linker(s), which may be the same or different. The one or more linker(s) may attach and/or bind (e.g., covalently or noncovalently) a molecular recognition element and/or a nucleic acid sequence to the solid support. For example, a linker may be used to attach or bind one or more molecular recognition element(s) to a solid support and/or the same or a different linker may be used to attach or bind one or more nucleic acid sequence(s) to the solid support. A "linker" as used herein refers to any molecule, moiety and/or functional group that can be used to attach or bind one component (e.g., a solid support) to another (e.g., a molecular recognition element). Example linkers include, but are not limited to, chemical moieties and/or compounds such as, e.g., amines (e.g., amine derivatives, isocyanates, isothiocyanates, iodoacetamides, azides, etc.), acids (e.g., acid derivatives N-hydroxysuccinimide esters, acid hydrazides, etc.), aldehydes, sulfonyl chlorides, sulfonyl hydrazides, epoxides, hydroxyl groups, thiol groups, and/or tnaleimides and/or biomolecules such as, e.g., proteins, peptides, DNA, and/or RNA. In some embodiments, the linker is a biamolecule that is a member of a specific binding pair, "Specific binding pair" and "ligand-receptor binding pair" are used interchangeably herein and refer to two different molecules, where one of the molecules has an area on the surface or in a cavity of the molecule that specifically attracts or binds to a particular spatial or polar organization of the other molecule, causing both molecules to have an affinity for each other. The members of the specific binding pair can be referred to as ligand and receptor (anti-ligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-a and tumor necrosis factor-receptor, and interferon and interferon receptor; avidin and biotin or antibiotin; antibody and antigen pairs; enzymes and substrates; drug and drug receptor; cell-surface antigen and lectin; two complementary nucleic acid strands; nucleic acid strands and complementary oligonucleotides; interleukin and interleukin receptor; and stimulating factors and their receptors such as granulocyte-macrophage colony stimulating factor (GMCSF) and GMCSF receptor and macrophage colony stimulating factor (MCSF) and MCSF receptor. Further exemplary linkers and/or chemistries that can be used to attach two components include, but are not limited to, photocleavable biotin, linkers providing a covalent bond between the solid support and the recognition element, avidin, Acrydite™ commercially available from Integrated DNA Technologies, Inc., adenylation, azide (NHS Ester), digoxigenin (NHS Ester), cholesterol-TEG, I-Linker™ commercially available from integrated DNA Technologies, Inc., Uni-Link™ Amino Modifier commercially available from Integrated DNA Technologies, Inc., 5' Hexynyl, 5-Oetadiynyi dU, Biotin dT, Biotin-TEG, Dual Biotin, Desthiabiotin-TEG, Thiol Modifier C3 S—S, dithiol, and/or thiol Modifier C6 S—S.

Any suitable coupling chemistry may be used to bind, a molecular recognition element and/or a nucleic acid sequence to a solid support. In some embodiments, the linker, molecular recognition element and/or nucleic acid sequence include a labile chemical bond that can be used to separate the molecular recognition element or a portion thereof from the solid support and/or to, separate the nucleic acid sequence or a portion thereof from the solid support. The labile chemical bond may be cleaved using various techniques including, but not limited to, the use of heat, light, and/or a chemical to cleave the labile chemical bond. For example, thermal energy may be applied to break or cleave a labile chemical bond or light may be applied to break a labile chemical bond (e.g., a photo-cleavable bond). Thermal heating may be accomplished by conductive contact with a hot surface, joule heating of a solution, resistive heating of a substrate that is adjacent the solid support, exposure to electromagnetic radiation and/or electromagnetic induction. In some embodiments, a labile chemical bond may be cleaved using ionizing radiation, a chemical agent, an enzyme, an electrochemical process, a change in pH, and/or other suitable cleaving operations. For example, a change in pH may be caused by electrochemical reactions occurring at the surface of a region including a solid support or a change in conditions may be directly or indirectly caused by an activation of an initiator reagent, which, itself may be activated by a physical change such as heat, light, electrochemical processes, change in pH, etc. In some embodiments, cleaving of a labile chemical bond may be performed prior to and/or during a PCR assay and/or reaction. In some embodiments, a labile chemical bond is cleaved to separate a nucleic acid sequence from the solid support so that a PCR can occur and/or be initiated. In some embodiments, a PCR reaction does not occur until a nucleic acid sequence (e.g., a forward primer and/or reverse primer) is released from the solid support to which it is attached. In some embodiments, a PCR reaction can occur while a nucleic acid sequence is attached to a solid support. In some embodiments, a component (e.g., a molecular recognition element and/or nucleic acid sequence) may be attached to a solid support using a compound, composition, and/or method as described in U.S. Pat. No. 9,617,589, the contents of which are incorporated herein by reference in their entirety.

In some embodiments, a molecular recognition element (e.g., antibody) and/or nucleic acid sequence (e.g., primer or oligonucleotide) is attached to a solid support via a photorleavable or heat labile bond. For example, in some embodiments, photocleavable biotin is used to attach a molecular recognition element and/or nucleic acid sequence to a solid support. In some embodiments, one or more attachment chemistries are used to attach a molecular recognition element and/or nucleic acid sequence to a solid support such as, but not, limited to, those utilizing a molecule with an affinity for an antibody such as, e.g., Protein A, Protein G, Protein A/G, Protein L, etc.

In some embodiments, a nucleic acid sequence (e.g., a forward primer) may be attached to a solid support by a covalent linkage, especially if hydrolysis probes or TaqMan probes are used for the detection chemistry, as the dye from the hydrolysis probe may still be detected even if the dsDNA amplicons are attached to the beads.

In some embodiments, a solid support includes a plurality of linkers and/or is coated with one or more linker(s). For example, a solid support may comprise streptavidin that is bound to and/or coated on at least a portion of the surface of the solid support, and one or more biotinylated molecular recognition element(s) and/or one or more biotinylated nucleic acid sequence(s) may be bound to the solid support via the binding of streptavidin and biotin. In some embodiments, a solid support (e.g., bead) comprises about 3.5 amol of streptavidin per solid support and each streptavidin binds about 1, 2, 3, or 4 biotinylated molecules. In some embodiments, the ratio of molecules of molecular recognition element to molecules of nucleic acid sequences present on a solid support is about 4:1, 3:1, 2:1, 1:1, 1:2, 1:3, or 1:4 (molecular recognition elements:nucleic acid sequences).

A solid support may comprise a molecular recognition element and/or nucleic acid sequence in an amount of about 1, 10, 50, 100, 200, 300, 400, 500, or 600 molecules (i.e., molecular recognition element(s) and/or nucleic acid sequence(s)) to about 1,000, 5.000, 10,000, 50,000, 100,000, 250,000, 500,000, 1,000,000, 10,000,000, 25,000,000, 50,000,000, 60,000,000 or more molecules. In some embodiments, a solid support comprises molecular recognition elements and/or nucleic acid sequences in an amount of about 10, 30, 50, 75, or 100 ymol to about 1, 2, 3, 4, 5, 6, 7, 8, 9, 10, 11, 12, 13, 14, or 15 fmol. In some embodiments, a solid support comprises molecular recognition elements and/or nucleic acid, sequences in an amount of about 0.1, 0.3, 0.5, 0.75, 1, 2, 3, 4, or 5 nmol to about 1, 5, 10, 15, 20, 25, 30, 35, or 40 amol. In some embodiments, a solid support comprises and/or binds a molecular recognition element in an amount of about 1 amol, in an amount in a range of about 1 zmol to about 100 amol, or in an amount in a range of about 100 ymol to about 10 fmol. In some embodiments, a solid support comprises and/or binds a nucleic acid sequence (e.g., a primer and/or single strand oligonucleotide) in an amount of about 3 amol, in an amount in a range of about 0.3 zmol to about 30 amol, or in an amount in a range of about 30 ymol to about 3 fmol.

A solid support may provide an assay and/or reaction well with a molecular recognition element present in an amount in a range of about 1 nM to about 1 mM and/or with a nucleic acid sequence present in an amount in a range of about 300 pM or 1 or 3 nM to about 300 μM or 3 mM. In some embodiments, a solid support may provide an assay and/or reaction well with a nucleic acid sequence (e.g., primer) present in an amount in a range of about 1 μM to about 100 nM. The concentration of the molecular recognition element and/or nucleic acid sequence may be the amount present on the solid support and/or released from the solid support. In some embodiments, the concentration of a molecular recognition element and/or nucleic acid sequence provided in an assay and/or reaction well by a solid support may be sufficient to perform or carry out an amplification process (e.g., PCR) and/or to detect a target.

In some embodiments, a nucleic acid sequence may be attached and/or bound to a solid support, optionally via a linker, and may have a length of about 5, 10, 20, or 25 nucleotides to about 30, 40, 50, 60, 70, 80, 90, 100, 150, 200, 250, 300, 350, 400, 450, or 500 nucleotides. In some embodiments, the nucleic acid sequence comprises at least five nucleotides to about 500 nucleotides (e.g., 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, the nucleic acid sequence is an oligonueleatide. In some embodiments, nucleic acid sequence is primer (e.g., a forward primer or a reverse primer), which may be used, far example, as a primer in a PCR assay, as a probe in a hybridization assay, and/or in a microarray. Primers useful in the present invention include, but are not limited to, those for amplification and/or detection. In some embodiments, the nucleic acid sequence comprises about 15 nucleotides to about 50 nucleotides or about 20 nucleotides to about 25 nucleotides. In some embodiments, a solid support of the present invention comprises at least one forward primer and/or at least one reverse primer. In some embodiments, a solid support of the present invention comprises a forward primer and does not comprise a reverse primer. In some embodiments, a solid support of the present invention comprises a forward primer and a reverse primer.

In some embodiments, a primer may be absorbed into a solid support (e.g., a hydrogel bead) such that the primer is mostly inside tine solid support and not exposed on the outside of the solid support (where a molecular recognition element (e.g., capture antibody) may be bound). Exemplary hydrogel beads include, but are not limited to, agarose beads (e.g., Sepharose beads).

A primer present on a solid support may be associated with a chemical species that prevents hybridization such as, e.g., certain nucleic acid sequences (optionally with modified bases) with a melting point higher than the temperature at which a detection reagent is incubated but lower than the annealing temperature at which PCR is performed. Alternatively, or in addition, peptides, proteins, RNA sequences, polymers, and/or other reagents may be used to reduce nonspecific binding and/or unwanted hybridization to the primers on the solid support.

In some embodiments, a solid support comprises a self-avoiding primer derived from one or more modified base(s) such as, for example, those available from Firebird and other sources. In some embodiments, a self-avoiding molecular recognition systems (SAMRS) is a forward primer and a nucleic acid tag of the detection reagent, and the reverse primer is normal DNA.

A forward primer and/or a reverse primer on a solid support of the present invention and/or a detection reagent of the present invention may be configured to bind certain components at the appropriate time. For example, in some embodiments, a primer (e.g., a forward primer) is prevented from binding with a nucleic acid tag of the detection reagent until after the first PCR cycle because the NA tag is single-stranded and the primer binding site does not exist until after the first PCR cycle. In some embodiments, a forward primer and reverse primer may be designed so that they are unavailable to base pair at lower temperatures (e.g., during incubation with the detection reagent), but become available at higher temperatures (e.g., at a time after excess detection reagent is washed away). In some embodiments, a forward primer and/or reverse primer on a solid support of the present invention may be double-stranded (e.g., via a duplex or a hairpin structure) and upon a denaturation step of PCR, the primer(s) becomes single stranded. The primer(s) may be designed so that the double-stranded structure (e.g., duplex or hairpin) does not form to a significant degree at the PCR annealing temperature as it may inhibit PCR. In some embodiments, a forward primer and/or reverse primer on a solid support of the present invention may become available after an enzymatic cleavage. For example, the primer may be part of a duplex and the competitor strand (reverse compliment to the primer) contains cleavable bonds. Degradation of the competitor strand into smaller portions may significantly the lower melting temperature so that it would not compete during PCR. For the cleavable bonds, the following nonexclusive examples may be used: photocleavable bonds, a specially-incorporated nucleotide that can be acted upon by an endonuclease or other enzyme, or RNA that can be acted upon by an RNAse. In some embodiments, the cleavage provides the primers with extendable 3' ends.

In some embodiments, a detection reagent of the present invention may be protected and/or designed to minimize hybridization to the primers on a solid support. For example, techniques similar to those, discussed above (e.g., a dsDNA duplex, hairpin structure) could be used so that the reverse primer binding site is already base paired.

According to some embodiments provided is a plurality of solid supports that comprise a first plurality of solid supports and a second plurality of solid supports. Each solid support in the first plurality of solid supports comprises; a first encoding agent (e.g., a dye) that provides a first encoding signal; a first nucleic acid sequence; and a first molecular recognition element (e.g., an antibody), and each solid support in the second plurality of solid supports comprises: a second encoding agent (e.g., a dye) that provides a second encoding signal; a second nucleic acid sequence; and a second molecular recognition element (e.g., an antibody). Solid supports in the first plurality of solid supports are distinguished and/or differentiated from solid supports in the second plurality of solid supports as the first encoding signal is different than the second encoding signal, the first nucleic acid sequence is different than the second nucleic acid sequence, and/or the first molecular recognition element is different than the second molecular recognition element.

According to some embodiments provided is a detection reagent that comprises a molecular recognition element (e.g., an antibody) and a nucleic acid sequence. The nucleic acid sequence of the detection reagent is also referred to herein as a "nucleic acid tag" or "tag". The detection reagent may bind to a first portion of a target and a solid support of the present invention may bind to a second portion of the target. In this manner, the detection reagent has a corresponding solid support in that it is paired with a solid support via the target. The nucleic acid tag for a detection reagent of the present invention has a portion that is configured to participate in a nucleic acid amplification process with a portion of the nucleic acid sequence attached (e.g., bound) to the corresponding solid support for the detection reagent. In some embodiments, a detection reagent of the present invention is a detection antibody comprising a nucleic acid tag.

The nucleic acid tag of the detection reagent may comprise about 20, 30, 40, 50, or 60 nucleotides to about 70, 80, 90, 100, 110, 120, 130, 140, 150, 160, 170, 180, 190, 200, 220, 240, 260, 280, or 300 nucleotides. In some embodiments, the nucleic acid tag comprises a hairpin loop.

In some embodiments, at least a portion of the nucleic acid tag is substantially identical to at least a portion of the nucleic acid sequence of the corresponding solid support for the detection reagent. In some embodiments, at least about 5 or more (e.g., 6, 7, 8, 9, 10, 15, 20, or more) sequential nucleotides in the nucleic acid tag are substantially identical to at least about 5 or more (e.g., 6, 7, 8, 9, 10, 15, 20, or more) sequential nucleotides in the nucleic acid sequence of the corresponding solid support for the detection reagent. In some embodiments, a sequence in the 5' region of the nucleic acid tag is substantially identical to a sequence in the nucleic acid molecule of the solid support. In some embodiments, a sequence in the 5' region of the nucleic acid tag is substantially identical to a nucleic acid sequence of the corresponding solid support for the detection reagent and/or a sequence in the 3' region of the nucleic acid tag is complementary to a reverse primer, which may optionally be present in a PCR master mix. In some embodiments, two or more detection reagents, which correspond to two or more different solid support sets, comprise a substantially identical sequence in the 3' region of the nucleic acid tag, and this sequence may be complementary to a reverse primer.

Referring now to FIG. 6, an exemplary complex according to embodiments of the present invention is shown with the complex including an encoded solid support, a target, and a detection reagent. The encoded solid support is an encoded bead that is functionalized with both a forward primer and an antibody (e.g., a capture antibody) that binds to a target. The detection reagent shown in FIG. 6 is an antibody comprising a nucleic acid sequence, and the antibody is bound to the target, thereby forming a complex of the present invention. The captured target is thus labeled with the detection antibody containing a unique nucleic acid sequence, and at least a portion of the nucleic acid sequence (i.e., nucleic acid tag) is amplified by the forward primer of the corresponding encoded bead, optionally when the forward primer is released from the bead, and a reverse primer provided in a PCR master mix. The PCR product can then be detected by fluorescence signal (e.g., from a dsDNA intercalating dye).

Detection reagents corresponding to solid supports in one solid support set or plurality each comprise the same nucleic acid tag. The nucleic acid tag is different for detection reagents that correspond to different solid supports. Referring again to FIG. 6, the nucleic acid tag of the detection reagent includes a sequence in the 5' region that is configured to participate in a nucleic acid amplification process with at least a portion of the forward primer. In addition, the nucleic acid tag includes a sequence in the 3' region that is complementary to a reverse primer and this nucleic acid sequence is also present in (and thus common to) different detection reagents that correspond to different solid supports as shown in FIG. 7. Accordingly, the nucleic acid tag may be amplified by two primers: a unique forward primer and a common reverse primer. The unique forward primer may be substantially identical to a sequence in the 5' region of the nucleic acid tag. A reverse primer may be complementary to a sequence in the 3' region of all nucleic acid tags and may be added to the PCR master mix.

In some embodiments, the nucleic acid sequence of the solid support and/or the nucleic acid tag of the detection reagent comprises single stranded DNA. In some embodiments, the nucleic acid sequence of the solid support and/or the nucleic acid tag of the detection reagent comprises double stranded DNA. In some embodiments, the nucleic acid sequence of the solid support and/or the nucleic acid tag of the detection reagent comprises RNA or hybridized DNA-RNA. In some embodiments, the nucleic acid sequence of the solid support and/or the nucleic acid tag of the detection reagent comprises one or more chemically modified base(s) such as, e.g., one or more chemically modified base(s) that are not usually found in nature. The one or more chemically modified base(s) may improve the specificity of a PCR reaction and/or reduce nonspecific binding between nucleic acid sequences (e.g., oligonucleotides).

The nucleic acid tag may be attached or bound to a molecular recognition element in any manner and/or to any portion of the molecular recognition element. In some embodiments, the nucleic acid tag is covalently or noncovalently attached to a molecular recognition element. In some embodiments, a linker is used to attach a nucleic acid tag to a molecular recognition element. The nucleic acid tag may be attached to one or more amino acid(s) of the molecular recognition element (e.g., antibody). In some embodiments, the molecular recognition element is an antibody or a fragment thereof and the nucleic acid tag may be attached (e.g., covalently attached) to the fragment crystallizable (Fc) region of the antibody or fragment thereof.

In some embodiments, the nucleic acid tag may be a chemically synthesized single-stranded DNA (ssDNA). In some embodiments, a double-stranded DNA (dsDNA) tag attached to a molecular recognition element provides a detection reagent that may provide reduced nonspecific binding. In some embodiments, hybridization of dsDNA to a primer bound to a solid support is mitigated by designing the complement strands (e.g., to the primer or to the nucleic acid tag) to ensure it remains annealed during an assay, optionally until its desired release. As one of skill in the art will recognize, DNA strands can undergo melting and annealing (fraying) at a rate determined by sequence, temperature, and the chemical environment. This fraying of the ends could increase nonspecific binding or undesired hybridization to other nucleic acid molecules (such as, e.g., primers or probes bound to the solid support). In order to prevent hybridization of the complement strand of a dsDNA tag to a forward primer bound to a solid support, the complement strand may be shorter, i.e., lacking the sequence complementary to the forward primer. In this case, the tag may be partially dsDNA and partially ssDNA.

In some embodiments, the nucleic acid tag may be a hairpin tag sequence and/or a sequence with CC clamps. A hairpin sequence and/or sequence with GC clamps may reduce fraying of the ends and/or undesirable hybridization during incubation with a detection reagent. In some embodiments, the nucleic acid tag may be an RNA sequence and reverse transcriptase maybe used. The RNA sequence may include an RNA hairpin with an internal structure that may prevent hybridization during sample capture.

In some embodiments, a nucleic acid tag may be encapsulated by a protein, membrane, micelle, peptide, bacteriophage, etc. such that it cannot hybridize to a nucleic acid sequence (e.g., primer) bound to a solid support until desired (e.g., after sealed in a reaction well).

In some embodiments, the nucleic acid tag comprises a restriction enzyme site. The nucleic acid tag comprising a restriction enzyme site may be designed such that an enzyme cleaves a hairpin or GC clamp and this may be used to release a nucleic acid sequence for efficient PCR analysis. In some embodiments, a nucleic acid tag comprises a photocleavable bond or a chemically cleavable disulfide linker, which may be used to release all or a portion of the nucleic acid tag from the detection reagent.

A nucleic acid tag of the present invention does not need to contain a unique region and a common region such as, for example, shown in FIG. 7. In some embodiments, the nucleic acid tag of the detection reagent comprises a sequence that is wholly or partially unique and a mixture of forward or reverse primers may be added to the master mix for such a sequence.

In some embodiments, the nucleic acid tag comprises at least one common region that is a conserved nucleic acid sequence in the nucleic acid tags of different detection reagents and that is large enough such that some or all of the sequence can be detected by amplification with one or more primer pair(s). A conserved nucleic acid sequence may be present in the 5' region and/or in the 3' region located outside of the unique region. The conserved region can be present in all of the nucleic acid tags for all of the two or more different detection reagents. Thus, the nucleic acid tags for different detection reagents may be designed so that they can be amplified by a unique primer pair and by a universal primer pair that is common to the nucleic acid tags of all the detection reagents. This embodiment may be useful for troubleshooting during assay development so that nonspecific binding and/or cross-reactivity can be easily visualized. In some embodiments, a nucleic acid tag of the present invention comprises at least two nucleic acid sequences, one that is amplified by a unique reverse primer and another that is amplified by a universal reverse primer.

A nucleic acid tag may be attached to a molecular recognition element to provide a detection reagent using any method known to those skilled in the art. In some embodiments, a nucleic acid tag is attached to a molecular recognition element using traditional chemical methods, click chemistry, genetic engineering, and/or molecular engineering methods.

In some embodiments, the molecular recognition element of a detection reagent of the present invention may be functionalized to a nanoparticle that is functionalized with a nucleic acid tag and optionally primers and/or probes that amplify a nucleic acid sequence bound to a solid support. However, in some embodiments, multiplexed primer sets in variable concentrations are avoided to reduce assay variance.

In some embodiments, when a detection reagent comprises a molecular recognition element that comprises nucleic acids, then the nucleic acid tag may be provided by all or a portion of the molecular recognition element. That is, the molecular recognition element itself may act as a nucleic acid tag.

According to some embodiments a plurality of detection reagents is provided that comprises a first plurality of detection reagents with each detection reagent in the first plurality comprising: a first molecular recognition element (e.g., an antibody) and a first nucleic acid tag; and a second plurality of detection reagents with each detection reagent in the second plurality comprising: a second molecular recognition element (e.g., an antibody) and a second nucleic acid tag; wherein the first and second nucleic acid tags each include a first portion and a second portion; and wherein the nucleic acid sequence of the first portion for the first nucleic acid tag is different than the nucleic acid sequence of the first portion for the second nucleic acid tag. In some embodiments, the nucleic acid sequence of the second portion for the first and second nucleic acid tags are the same or substantially identical. In some embodiments, the first portion for the first and second nucleic acid tags is in the 5' region of the respective tag and second portion is in the 3' region of the respective tag. The first nucleic acid tag may be attached to (e.g., linked to, bound to, and/or fused with) the first molecular recognition element and the second nucleic acid tag may be attached to (e.g., linked to, bound to, and/or fused with) the second molecular recognition element.

According to some embodiments provided is a composition, kit, device, and/or system comprising a solid support as described herein and/or, a detection reagent as described herein. The solid support and detection reagent, may form a complex when a target is present that corresponds to the solid support and detection reagent. The composition, kit, device, and/or system may comprise a plurality of solid supports optionally comprising two or more different encoded solid supports and a plurality of detection reagents optionally comprising two or more different detection reagents.

In some embodiments, bead sets may be prepared by encoding each set with a unique dye or unique combination of fluorescent dyes as shown by bead "A", "B" and "C" in FIG. 7. For example, bead set "A" may be stained with a red fluorescing dye while bead set "B" is stained with a blue fluorescing dye. In some embodiments, all sets are functionalized with streptavidin before each set is incubated with a different, biotinylated capture antibody for a particular target molecule. Finally, each set is incubated with a unique biotinylated primer (e.g., forward primer). In some embodiments, detection reagents are prepared by covalently attaching a unique nucleic acid tag to a detection antibody for each target. In some embodiments, the tag is a 60 nucleotide (nt), single stranded DNA (ssDNA) that has a unique sequence at the 5' end or region and a common sequence at the 3' end or region that is conserved amongst all the tags. Each tag is amplified by two primers: a forward primer (that is different for each tag) and a common reverse primer. In some embodiments, the forward primer may comprise a sequence that is identical or substantially identical to a sequence in the 5' region or at the 5' end of the tag attached to the detection antibody. Alternatively, the 3' end of the tag can be attached to the detection antibody. In some embodiments, a reverse primer that is complementary to the conserved 3' end or region of all tags may be added to the PCR master mix. In this manner, bead set A will carry both capture antibody A and forward primer A that can only amplify the nucleic acid tag A that is linked to detection antibody A. Bead set B will carry both capture antibody B and forward primer B that can only amplify the nucleic acid tag B that is linked to detection antibody B. The primer added to the master mix serves as the reverse primer for both nucleic acid tag A and nucleic acid tag B since the 3' end or region of the tags includes a conserved sequence.

In some embodiments, solid supports of the present invention do not contain a complementary sequence that can hybridize to a nucleic acid tag. Such hybridization may result in significant pull-down of the detection reagent from the incubation mixture in the absence of a target, creating a very high background signal. For this reason, in some embodiments, only the forward primer is attached to a solid support, since the forward primer is identical or substantially identical in sequence (not complementary) to the 5' end or region of the tag. The reverse primer, which is complementary to the tag, may be added to the PCR master mix so that PCR can be performed.

In some embodiments, an assay is performed in the presence of a mixture of solid supports for different targets and the solid supports are incubated with a sample. The solid supports may capture a target, and the sample matrix may be washed away. The solid supports may then be incubated with a mixture of multiple detection antibody reagents corresponding to the solid support in order to label the captured target to form a complex. The complexes may be washed and/or loaded into an array (e.g., a microwell array that is sized such that most reaction wells contain only a single bead). A PCR master mix containing a common reverse primer that is complementary to the 3' end or region of all the tags may be added, optionally before each reaction is fluidically isolated, e.g., by sealing with an immiscible oil. During the denaturation step of PCR, the forward primers attached to the solid supports may be released into the isolated reaction wells so that each well now contains a complete PCR primer set. For example, wells containing bead type A will be PCR positive if detection antibody conjugate A is present, and wells containing bead type B will be PCR positive if detection antibody conjugate B is present.

However, reactions containing bead type A and nonspecifi-
cally bound detection antibody conjugate B will not be PCR
positive, as the primer carried by bead type A cannot amplify
the nucleic acid tag on detection antibody conjugate B (FIG.
8). In this way, iPCR assays optimized as singleplex reac-
tions may require less re-optimization when multiplexed
because the total detection antibody concentration that can
be amplified and/or detected by each bead set does not
change as additional targets are added to the assay.

In some embodiments, a method of the present invention
captures and/or results in the binding of about 0 to about
10,000,000 detection reagents as complexes with their cor-
responding solid support, For example a method of the
present invention may capture and/or result in the binding of
about 0, 1, 2, 3, 4, 5, 6, 7, 8, 9, 10, 12, 15, 20, 25, 30, 35,
40, 45, 50, 55, 60, 70, 80, 90, 100, 120, 140, 160, 180, 200,
250, 300, 350, 400, 500, 600, 700, 800, 900, 1,000, 1,200,
1,400, 1,600, 2,000, 2,200, 2,500, 2,750, 3,000 , 3,500,
4,000, 4,500, or 5,000 to about 10,000, 25,000, 50,000,
75,000, 100,000, 200,000, 300,000, 400,000, 500,000, 600,
000, 700,000, 800,000, 900,000, 1,000,000, 5,000,000, or
10,000,000 detection reagents as complexes with their cor-
responding solid support.

In some embodiments, a composition, kit, device, and/or
system of the present invention further comprises an ampli-
fication agent. Exemplary amplification agents include, but
are not limited to, a reverse primer, a ssDNA splint and
ligase, etc. In some embodiments, the amplification agent
has a nucleic acid sequence that is complementary to at least
a portion of the nucleic acid sequence of the detection
reagent and solid support, optionally wherein the portion of
the nucleic acid sequence is in the 3' region of the nucleic
acid tag. The amplification agent may be separate from the
solid support and/or detection reagent. In some embodi-
ments, the amplification agent is attached to a solid support,
optionally wherein the amplification agent is biotinylated.

A solid support of the present invention and its corre-
sponding detection reagent may be separately stored in a
composition, kit, device, and/or system of the present inven-
tion. In some embodiments, a detection reagent of the
present invention and an amplification agent are separately
stored in a composition, kit, device, and/or system of the
present invention. In some embodiments, a solid support of
the present invention and an amplification agent are sepa-
rately stored when the amplification agent is present and is
not attached to the solid support.

According to some embodiments provided is a method of
detecting a target in a sample. The method may comprise
combining a solid support of the present invention and a
sample comprising the target to form a first composition
comprising a target-bound solid support.

"Combining" and "combine" as used herein refer to
bringing two or more components into sufficient proximity
and/or contact to bind and/or react, optionally when under
suitable conditions. A detection reagent of the present inven-
tion may be combined with the target-bound solid support to
form a complex comprising the solid support, target, and the
detection reagent, wherein the detection reagent comprises a
molecular recognition element, which binds to the target,
and a nucleic acid tag. At least a portion of the nucleic acid
tag and at least a portion of the nucleic acid sequence bound
to the solid support are configured to participate in a nucleic
acid amplification process. At least a portion of the nucleic
acid tag is amplified, thereby allowing for detection of the
target in the sample. Any suitable method of amplification
may be used and/or performed such as, but not limited to,
PCR and/or rolling circle amplification (RCA).

In some embodiments, the method may comprise one or
more washing step(s), optionally using an aqueous solution.
The one or more washing step(s) may be performed to wash
the target-bound solid support and/or to wash the complex.
The one or more washing step(s) may remove unreacted
and/or non-bound components and/or those non-specifically
bound to the complex.

In some embodiments, an amplification agent is used in a
method of the present invention. The method may comprise
combining and/or reacting the amplification agent and a
complex comprising the solid support, target, and detection
reagent. Prior to, during, and/or after the step of combining
the amplification agent and the complex, the amplification
agent may be released from the solid support, when the
amplification agent is attached to a solid support. In some
embodiments, the amplification agent remains on the solid
support. In some embodiments, the amplification agent is
not attached to a solid support and is added to a composition
comprising the complex.

In some embodiments, the amplification agent is a nucleic
acid sequence (e.g., a primer), which may be released from
a solid support optionally prior to an amplification step. In
some embodiments, at least a portion of the nucleic acid
sequence bound to and/or released from the solid support is
amplified. In some embodiments, the amplification agent
comprises a ssDNA splint and ligase, which react under
suitable conditions to ligate two oligonucleotides together.
In some embodiments, a solid support of the present inven-
tion comprises an oligonocleotide (e.g., a ssDNA oligo) and
a detection reagent of the present invention comprises an
oligonucleotide (e.g., a ssDNA oligo), and when in the
presence of a ssDNA splint and ligase and suitable condi-
tions (e.g., when the oligos are in close proximity to each
other such as, e.g., when each is bound to the same target)
the two oligonucleotides are ligated and/or extended and
then at least a portion of the oligonucleotides may be
amplified. In some embodiments, a solid support of the
present invention comprises an oligonucleotide (e.g., a
ssDNA oligo) and a detection reagent of the present inven-
tion comprises an oligonucleotide (e.g., an oligo having, a 3'
overhang that can hybridize to the ssDNA oligo of the solid
support), and when in close proximity to each other such as,
e.g., when each is bound to the same target, the two
oligonucleotides hybridize, are extended, and then at least a
portion of the oligonucleotides may be amplified.

In some embodiments, a detection reagent of the present
invention is present in a composition including the corre-
sponding solid support of the present invention when a target
and the solid support are combined. In some embodiments,
a detection reagent of the present invention, its correspond-
ing solid support of the present invention, and a target, are
combined at the same time.

A method of the present invention may comprise ampli-
fying one or more nucleic acid sequences that are the same
and/or different. In some embodiments, a method of the
present invention comprises a polymerase chain reaction
(PCR). In some embodiments, a method of the present
invention comprises amplifying at least a portion of the
nucleic acid tag of the detection reagent. In some embodi-
ments, amplifying at least a portion of the nucleic acid tag
of the detection reagent is carried out using PCR. In some
embodiments, amplifying at least a portion of the nucleic
acid tag of the detection reagent does not involve PCR and
another nucleic acid amplification technique is used such as,
but not limited to, loop-mediated isothermal amplification
(LAMP), rolling circle amplification, strand-displacement
amplification, transcription-mediated amplification, and/or nucleic acid circuits, where an enzymatically degraded tag can start a chain reaction driven by hybridization.

In some embodiments, a method of the present invention is carried out using a proximity ligation assay (PLA). In some embodiments, a method of the present invention is carried out using a Binding Induced DNA Amplification (BINDA), Proximity Extension Assay (PEA), and/or triple PLA. In some embodiments, a method of the present invention is a multiplexed assay (e.g., an imrnuno-polymerase chain reaction (iPCR) assay) that is performed in a microfluidic device comprising a plurality of wells and the method further comprises isolating the solid support from one or more additional solid supports and in at least one well of the plurality wells.

The microfluidic device may or may not comprise a rigid or solid microwell array. In some embodiments, a solid support of the present invention may be isolated in droplets of aqueous PCR master mix in an immiscible oil (such as, e.g., those used in emulsion PCR, the BioRad Digital Droplet PCR system, the RainDance PCR system, or the technique known as BEaMing). In some embodiments, a forward primer is bound (e.g., tethered) to a solid support (e.g., bead) of the present invention via a covalent linkage or multiple biotin groups so that the signal can be readout by a flow cytometer after breaking the emulsion. Certain isothermal amplification techniques may be used in an emulsion/droplet format, or in bulk solution if the amplicons remain attached to the solid support. In some embodiments, a substrate, device, and/or method of the present invention may include, but is not limited to, one (e.g., a substrate, device and/or method) as described in U.S. Application Publication No. 2015/0211048, International Application No. PCT/US2016/042913, International Application No. PCT/US2016/043463, and International Application No. PCT/US2016/055407, the contents of each of which are incorporated herein by reference in their entirety. In some embodiments, a method of the present invention comprises a method of delivering reagents and/or targets into reaction wells using beads (e.g., superparamagnetic beads), such as described, for example, in U.S. Application Publication No. 2015/0211048 and International Application No. PCT/US2016/042913, the contents of each of which are incorporated herein by reference in their entirety.

In some embodiments, a compound, composition, kit, system, device, and/or method of the present invention may be used to perform any suitable reaction such as, but not limited to, assays involving biomolecules such as, e.g., PCR reactions; spatial array-based assays such as, e.g., reconfigurable multi-element diagnostic (ReMeDx) assays, single-plex reactions in a compact array (SiRCA); assays including aqueous reaction compositions; assays performed on plastic substrates, and/or assays described in International Publication No. WO 2013/176767, the contents of which are incorporated herein by reference.

In some embodiments, a method of the present invention comprises preparing a solid support of the present invention. A solid support of the present invention may be formed by contacting a solid support (optionally including one or more linker(s)) with a molecular recognition element and a nucleic acid sequence at the same time and/or at different times. In some embodiments, the molecular recognition element and nucleic acid sequence may be added at separate times to aid in providing a plurality of beads having substantially the same number (i.e., within ±20%) of molecular recognition elements and nucleic acid sequences on each respective bead in the plurality. In some embodiments, a method of preparing a solid support of the present invention includes contacting the solid support with one or more filler(s), such as, but not limited to, biotin, a biotinylated polymer, a biotinylated nucleic acid polymer, a biotinylated carbohydrate, a biotinylated quantum dot or other nanoparticle, biotinylated peptide, and/or a biotinylated protein. A filler may aid in controlling the amount of molecular recognition elements and/or nucleic acid sequences added to a solid support and/or may aid in reducing nonspecific binding during an assay.

In some embodiments, undesirable hybridization of a detection reagent to a nucleic acid sequence (e.g., primer) attached to a solid support may be reduced by using toe-hold displacement primers, hairpin primers, partially digestible hairpin primers, and/or blocking NA sequences. Primers may be tethered to the solid support at 5' and/or 3' ends or both. 5' and 3' ends. In some embodiments, double stranded primers may be used if suitable conditions are provided.

In some embodiments, incubation conditions and/or amplification conditions may be controlled in a method of the present invention such that hybridization of the detection reagent to the nucleic acid sequence attached to the solid support is not favored, but PCR amplification can still occur later during the detection stage of the method. For example, low melting point primers may be used under incubation conditions that favor the melted state (e.g., low salt or the addition of betaine) such that the primers do not hybridize to the detection reagent. However, conditions that favor a higher melting point could be used during PCR (e.g., higher salt or the removal of betaine) so that the primers can efficiently amplify a nucleic acid sequence of the detection reagent.

A target may be detected in a method of the present invention using any method known to those of skill in the at such as, for example, by visual observation and/or a chemical or biochemical assay. In some embodiments, a method of the present invention comprises detecting a target by detecting an assay signal. The assay signal may be, for example, a fluorescence signal such as, e.g., from a dsDNA intercalating dye and/or from hydrolysis of a probe containing a quencher and a dye.

In some embodiments, fluorescence is used for detection. In some embodiments, a method of the present invention includes and/or provides a fluorescence readout. In some embodiments, a method of the present invention includes and/or provides an electronic readout by hybridization of the amplicon to a solid-state sensor, sequencing of the amplicon by methods such as pyrosequencing, and/or formation of a precipitate such as that found during LAMP amplification.

Figure 5:
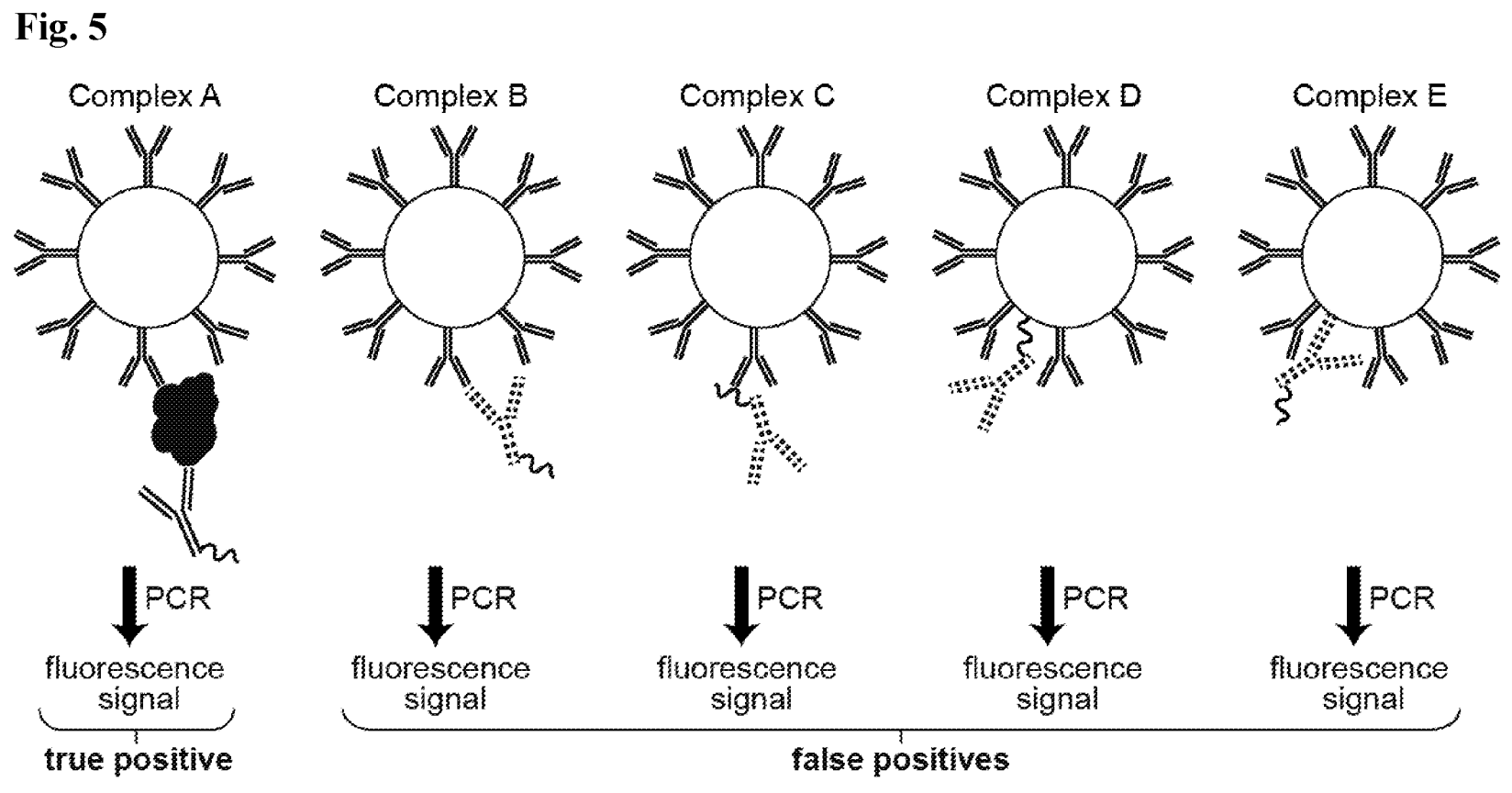

A method of the present invention may improve the specificity of an assay and/or may reduce the background signal for an assay. In some embodiments, a method of the present invention reduces the observed cross-reactivity between a solid support and a non-target molecule (e.g., the wrong antigen). "Observed cross-reactivity" as used herein refers to a detected signal that is associated with interactions between a solid support and a non-target molecule (e.g., the wrong antigen). In some embodiments, the detected signal may be visually observed. In some embodiments, a method of the present invention reduces the observed nonspecific binding of a solid support, such as, e.g., the fluorescence signal observed with false positives as shown in FIG. 5. In some embodiments, a method of the present invention improves signal to noise for an assay, improves sensitivity for an assay, and/or reduces the observed cross-reactivity for an assay. In some embodiments, a compound, composition, device, kit, system, and/or method of the present invention improves a multiplexed immuno-PCR (iPCR) assay.

In some embodiments, the observed cross-reactivity and/ or background signal for a target may be reduced by using different nucleic acid sequences for each target and/or to perform multiplexed, probe-based qPCR, where each probe is labeled with a spectrally-distinct fluorescent dye. In this case, the fluorescence increase observed from the hydrolysis of a probe can be referenced to the encoding of the bead to determine whether or not the correct complex was formed. In some embodiments, the sequences of the NA tags used in the detection reagents are carefully chosen such that the amplicons resulting from correct PCR amplification will have discrete melting points, optionally different melting points, such that they can be distinguished from nonspecific amplification products and optionally distinguished from one another. The use of different melting point amplicons can be used as a means of encoding to differentiate one bead population from, another and/or as a means of corroborating an encoding signal. A method of the present invention may reduce background signal for an assay by about 0.5, 1, 1.5, 2, 2.5, or 3 orders of magnitude compared to a control method (e.g., iPCR using known solid supports and detection reagents).

A compound, composition, kit, device, system, and/or method of the present invention may be used in a multiplexed immunoassay panel. Some embodiments of the present invention may useful in qualitative and/or quantitative medical and/or veterinary diagnostic testing, forensic testing, the identification of biological hazardous materials, environmental monitoring, research and development, and/ or the like. In some embodiments, the ability to multiplex molecular recognition element (e.g., antibody) pairs that would otherwise show high levels of cross-reactivity may enable new diagnostic tests that are currently unrealized.

The present invention is explained in greater detail in the following non-limiting examples.

EXAMPLES

Example 1

Single-molecule, bead-based immunoassays were developed using solid supports and detection reagents as described herein (referred to as "Protein SiRCA technology"). These assays were compared to analogous iPCR assays to show how Protein SiRCA technology can reduce background from nonspecific binding and antibody cross-reactivity.

Figure 1:
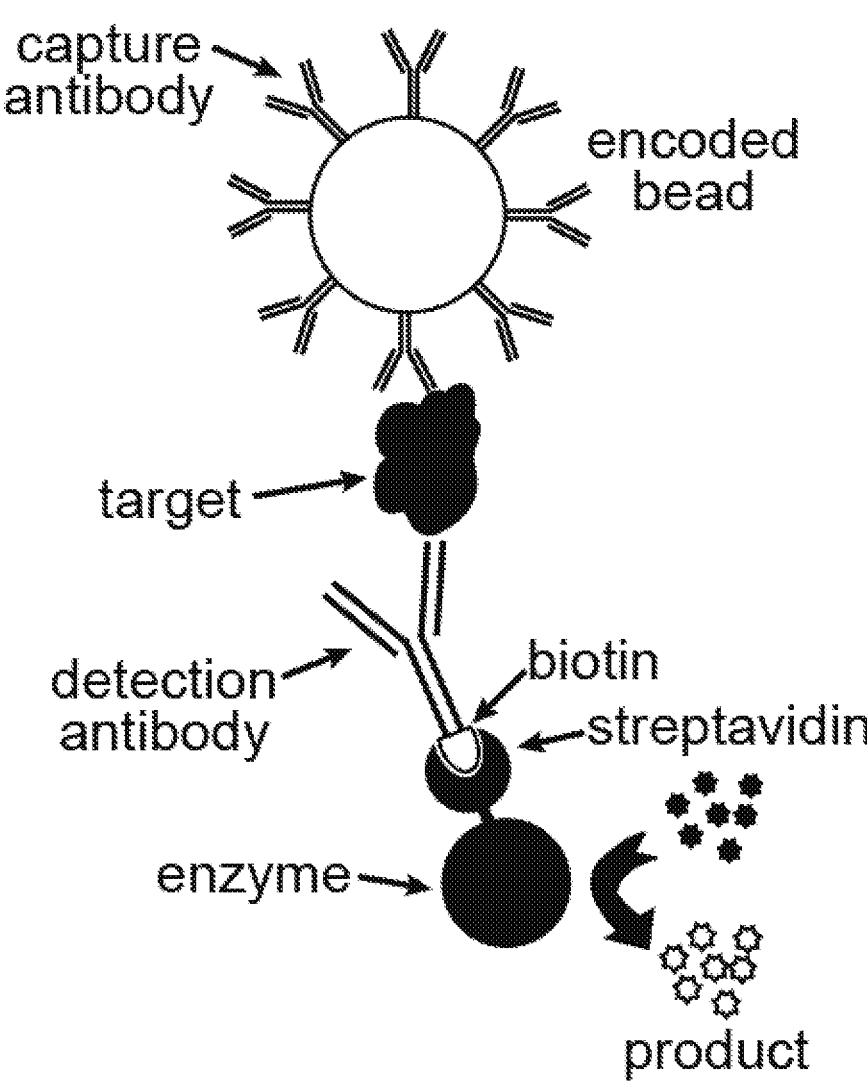
FIG. 1 is a schematic illustration of a complex formed from example affinity reagent pairs for use in ELISA.
Figure 2:
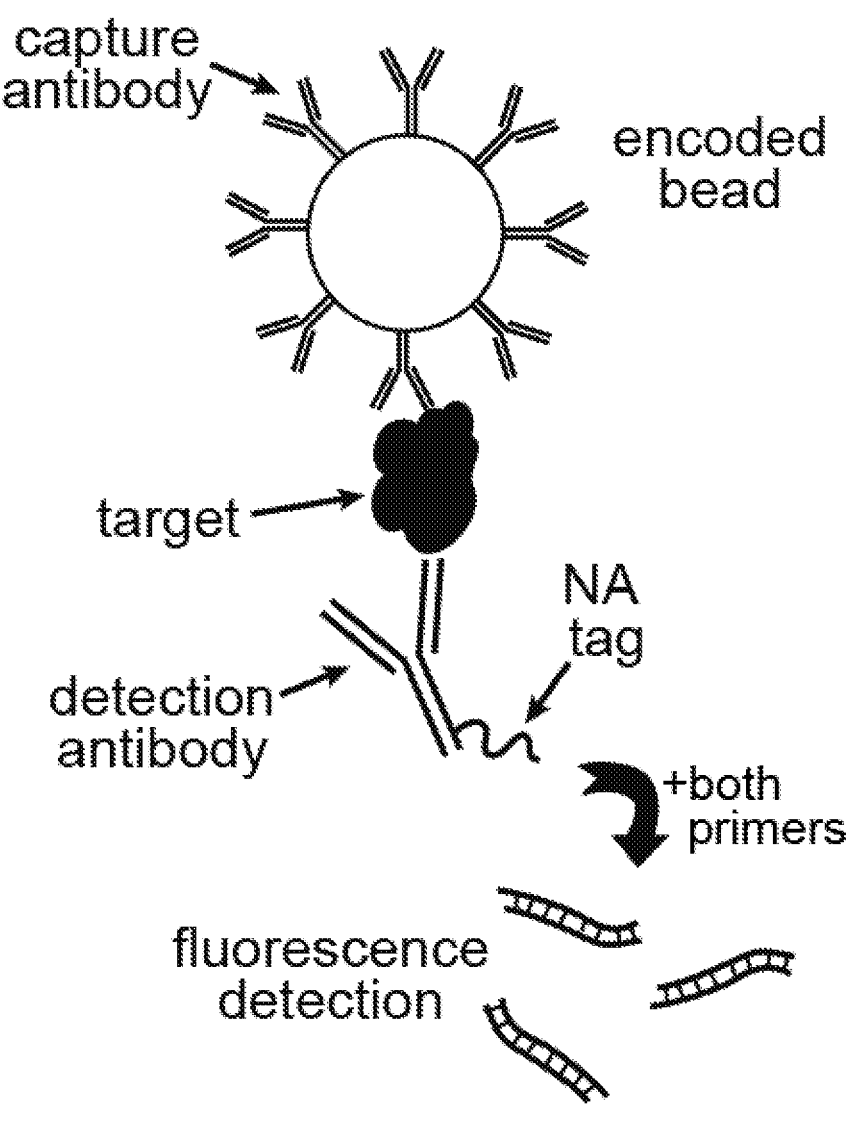
FIG. 2 is a schematic illustration of a complex formed from example affinity reagent pairs for use in iPCR.
Figure 3:
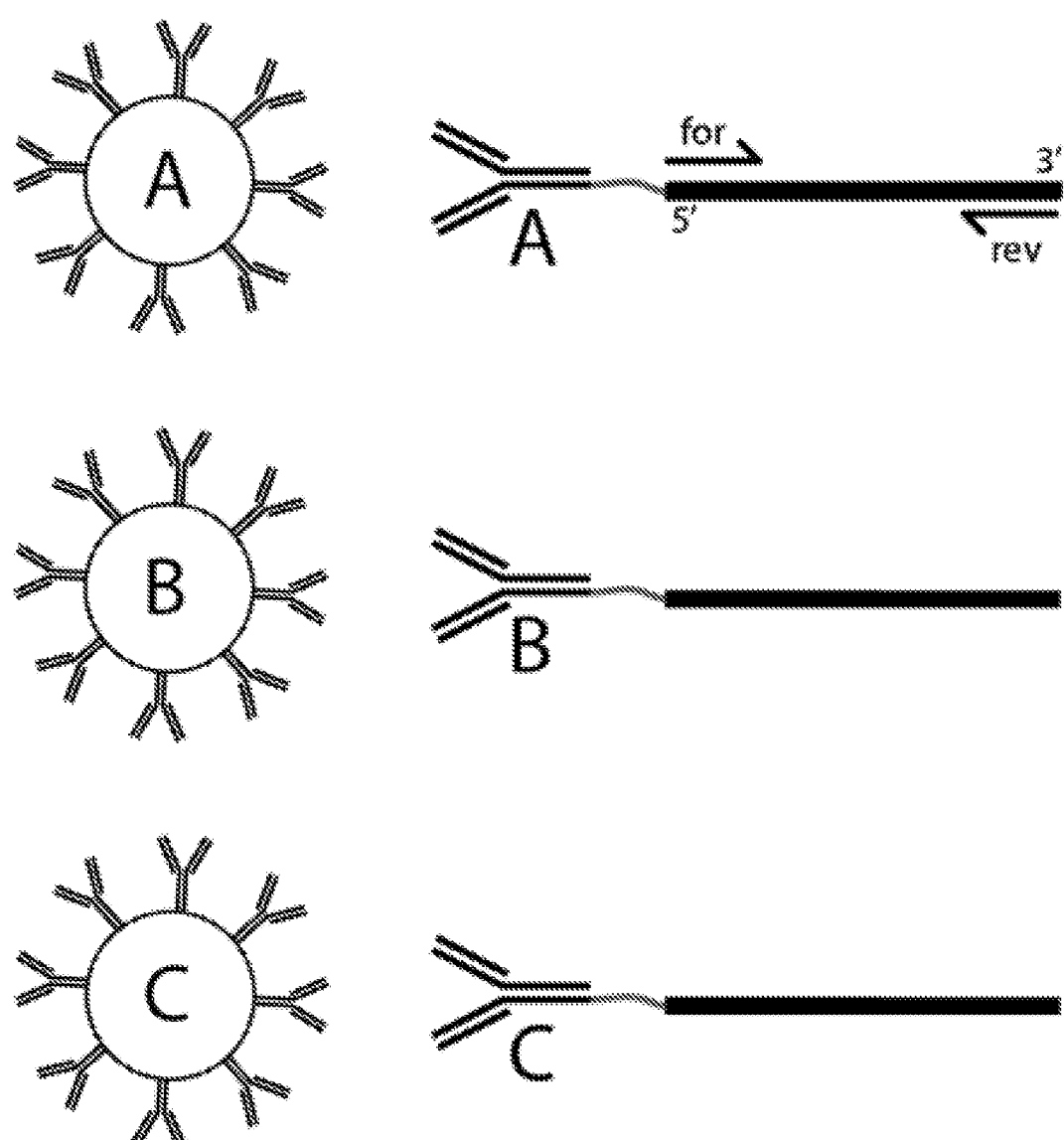
FIG. 3 is a schematic illustration of three different encoded, bead sets that are functionalized with separate capture antibodies and each bead set corresponds to a different detection antibody.
Figure 4:
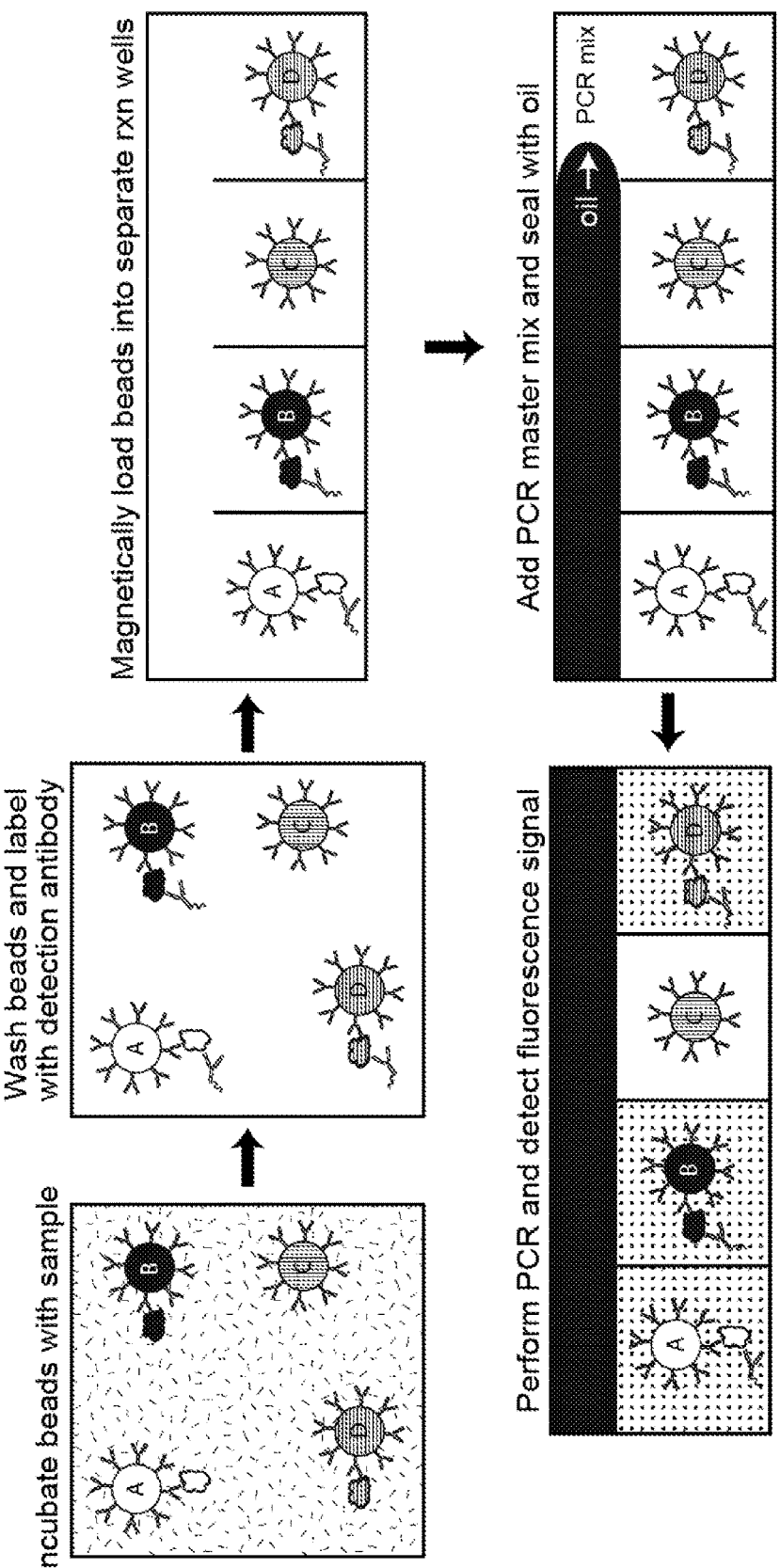
FIG. 4 is a schematic illustration of example method steps in a bead-based iPCR assay.

First, iPCR assays reagents were prepared. Bead sets for the cytokines IL-6, IL-7, IL-8, IL-10, and TNF-α were prepared by functionalizing 3 μm ProMag COOH-modified superparamagnetic beads with encoding dyes and capture antibodies. Detection antibody conjugates were made by attaching the same 60 nt, ssDNA tag to the relevant detection antibodies (FIG. 3) using the TriLink Biotechnologies Protein-Oligo Conjugation Kit. The iPCR assays were performed as shown in FIG. 4. Singleplex assays showed excellent sensitivity (FIG. 9A). In a 5-plex assay, measurements taken near the limit of detection (LOD), typically at or below about 1 pg/mL, show excellent sensitivity for most bead sets (FIG. 9B). However, upon multiplexing, the background signal increased significantly for all bead sets, especially for IL-8 (FIG. 9B and FIG. 9C).

Protein SiRCA beads were prepared by incubating streptavidin-coated Dynabeads with biotinylated capture antibody (FIG. 10). Antibodies were biotinylated in house using the TriLink Biotechnologies Chromalink Biotin Antibody Labeling Kit. The antibody-labeled beads were then incubated, with biotinylated forward primers that were covalently labeled with a fluorescent dye (FIG. 10) to encode the beads. Three sets of beads were prepared for cytokines IL-7, IL-8, and IL-10. A plot of the fluorescence intensity in the two encoding wavelengths for representative beads from each set is shown in FIG. 11. The encoding clusters for three iPCR beads with covalently attached dyes are also shown in FIG. 11. The tight clustering of each bead set allowed for accurate identification of each bead type in multiplexed experiments.

The percent positives of the Protein SiRCA beads was compared to the conventional iPCR beads in singleplex assays. The iPCR beads differ from Protein SiRCA beads in that the iPCR beads are not functionalized with streptavidin or coated with primers; they are covalently linked to encoding dyes and capture antibodies. The iPCR and Protein SiRCA beads for each target were incubated with either serum (blanks) or 90 fM of the target cytokine in serum (positive control). As the goal of this initial test was to determine the sensitivity or activity of the capture antibodies on the different assay beads, each bead set was incubated with the appropriate antibody conjugate developed for iPCR. (i.e. all detection conjugates had the same NA tag). Both primers were added to the PCR master mix. FIG. 12 shows the resulting signal for serum blanks and 90 fM of each cytokine. In general, Protein SiRCA beads behaved very similarly to iPCR beads in terms of signal to background, with the Protein SiRCA beads showing slightly higher signal and slightly higher background for these assays.

Next, detection antibody conjugates were prepared for Protein SiRCA. In iPCR, the same NA tag is used for each antibody conjugate. In Protein SiRCA, a different NA tag is used for each conjugate, as shown in FIG. 7. iPCR beads, which lack forward primers, were used in singleplex assays to compare the activity of the iPCR and Protein SiRCA conjugates. As such, primers for each tag were added to the master mix of each singleplex assay. Comparisons of the activity of the detection antibody conjugates in otherwise identical experiments showed that the sensitivity of all the Protein SiRCA conjugates was lower than the iPCR conjugates (FIG. 13). Characterization of the conjugates revealed that the Protein SiRCA antibodies were all under-labeled so that a significant proportion of the antibodies lacked a NA tag. These tagless antibodies can bind captured target molecule but do not produce a detectable (transducible) PCR signal. The differences in labeling efficiency between the iPCR and Protein SiRCA conjugates are likely due to batch variability of the purchased antibody stocks or aging reagents in the conjugation kit (TriLink Biotechnologies Protein-Oligo Conjugation Kit), as the iPCR and Protein SiRCA conjugates were prepared at different times. The observed differences between the conjugates is likely due to variability in preparation of antibody conjugates and is not an inherent characteristic of Protein SiRCA conjugates.

In order to account for the differences in the bead type, encoding scheme, antibody attachment to the beads, primer delivery, antibody conjugate labeling efficiency, and the PCR amplification efficiency of different NA tag sequences, baseline singleplex assays were performed for iPCR and Protein SiRCA (FIG. 14). The background signal for IL-7 and IL-8 in singleplex assays are slightly higher in Protein SiRCA, but the IL-10 Protein SiRCA has a lower background signal.

Next, three-plex iPCR assays containing iPCR beads for IL-7, IL-8, and IL-10 were performed using the three iPCR antibody conjugates. Beads for all three cytokines were mixed together and then incubated with buffer (blank) or 90 fM of each cytokine. A single set of forward and reverse printers for the common iPCR NA tag were provided in the PCR master mix. As anticipated from earlier works IL-8 showed a very high background signal; such a high percentage of positive wells indicates that there is likely several nonspecifically bound detection antibody complexes per bead. When either 90 fM IL-7 or IL-10 were spiked into the sample buffer, a significant increase in assay signal was observed in the appropriate bead sets. However, the addition of 90 fM IL-8 to the sample buffer did not result in a significant signal increase over background in IL-8 beads, indicating that this concentration was below the limit of detection in the three-plex iPCR assay (FIG. 15). A comparison chart of the four different assay conditions (blank and 90 fM of each cytokine) for each bead type is shown in FIG. 15e. The high signal from the IL-8 beads is likely due to nonspecific binding of other detection antibody conjugates.

The same three-plea assays were repeated using Protein SiRCA beads and detection antibody conjugates for IL-7, IL-8, and IL-10. Beads for all three cytokines were mixed together and then incubated with buffer (blank) or 90 fM of each cytokine (FIG. 16). Only the common reverse primer was provided in, the PCR master mix, because the unique forward primer for each conjugate tag was delivered to the well by the bead itself. A comparison chart showing the signal from each bead set for the four experiments (blank and 90 fM of each cytokine) is shown in FIG. 16. A discernable increase in signal over the background can be seen for all beads when their respective analytes are present.

A direct comparison of iPCR and Protein SiRCA assays is shown in FIG. 17. For the singleplex assay data, IL-7 shows a lower signal to background in Protein SiRCA compared to iPCR, likely due to issues with the Protein SiRCA antibody conjugate. IL-10 shows a significant improvement in signal to background in Protein SiRCA compared to iPCR. However, the most significant improvement can be seen in the IL-8 beads. The background signal of the Protein SiRCA IL-8 beads is more than an order of magnitude lower than that seen in iPCR, allowing for sufficient signal to background to easily discern the difference between 90 fM IL-8 and the blank.

The foregoing is illustrative of the present invention and is not to be construed as limiting thereof. The invention is, defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A kit comprising:
(i) a solid support, wherein the solid support comprises:
(a) an encoding agent;
(b) a first nucleic acid sequence, wherein the first nucleic acid sequence comprises a primer that hybridizes to the complement of a second nucleic acid sequence; and
(c) a first molecular recognition element, wherein the first molecular recognition element comprises an antibody or fragment thereof, aptamer, modified aptamer, peptide, protein, carbohydrate, and/or combinations thereof,
wherein the first nucleic acid sequence is attached to the solid support via a photocleavable or heat labile bond; and wherein the solid support does not comprise a primer that hybridizes to the second nucleic acid sequence; and
(ii) a detection reagent comprising a second molecular recognition element, wherein the second molecular recognition element comprises an antibody or fragment thereof, aptamer, modified aptamer, peptide, protein, carbohydrate, and/or combinations thereof, and the second nucleic acid sequence, wherein the second nucleic acid sequence comprises a nucleic acid tag comprising at least a first portion and a second portion, wherein the first portion of the second nucleic acid sequence is substantially identical to the primer in the first nucleic acid sequence,
wherein the first nucleic acid sequence and second nucleic acid sequence comprise single stranded-DNA; and
wherein the primer in the first nucleic acid sequence and at least the first portion of the second nucleic acid sequence are configured to participate in a nucleic acid amplification process, wherein the nucleic acid amplification process is polymerase chain reaction (PCR) configured to amplify the nucleic acid tag.

2. The kit of claim 1, wherein the solid support further comprises a linker and the linker is on the surface of the solid support and wherein the first molecular recognition element and/or the first nucleic acid sequence is/are attached to the linker.

3. The kit of claim 1, wherein the first nucleic acid sequence and/or the first molecular recognition element is/are attached to the solid support via a heat labile bond.

4. The kit of claim 1, wherein the first nucleic acid sequence comprises about 10 nucleotides to about 60 nucleotides.

5. The kit of claim 1, wherein the second nucleic acid sequence comprises about 20 nucleotides to about 300 nucleotides.

6. The kit of claim 1, wherein the second nucleic acid sequence is covalently attached to the second molecular recognition element.

7. The kit of claim 1, further comprising an amplification agent.

8. The kit of claim 7, wherein the amplification agent has a primer that (i) hybridizes to the second nucleic acid sequence and (ii) is complementary to the second portion of the second nucleic acid sequence.

9. The kit of claim 8, wherein the second portion of the second nucleic acid sequence is in the 3' region of the second nucleic acid sequence.

10. The kit of claim 1, wherein the first portion of the second nucleic acid sequence comprises at least 5 nucleotides and the primer in the first nucleic acid sequence comprises at least 5 nucleotides.

11. The kit of claim 1, wherein the first portion of the second nucleic acid sequence is present in the 5' region of the second nucleic acid sequence.

12. The kit of claim 1, wherein the second molecular recognition element is an antibody and the second nucleic acid sequence is attached to one or more amino acid(s) of the antibody.

13. The kit of claim 12, wherein the second nucleic acid sequence is covalently attached to the fragment crystallizable (Fc) region of the antibody.

14. The kit of claim 1, wherein the first molecular recognition element is attached to the solid support via a photocleavable or heat labile bond.

* * * * *